(12) United States Patent
Ogawa et al.

(10) Patent No.: US 7,126,000 B2
(45) Date of Patent: Oct. 24, 2006

(54) METHOD OF SYNTHESIZING CAMPTOTHECIN-RELATING COMPOUNDS

(75) Inventors: Takanori Ogawa, Tokyo (JP); Hiroyuki Nishiyama, Tokyo (JP); Miyuki Uchida, Tokyo (JP); Seigo Sawada, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 146 days.

(21) Appl. No.: 10/467,987

(22) PCT Filed: Feb. 21, 2002

(86) PCT No.: PCT/JP02/01538

§ 371 (c)(1),
(2), (4) Date: Dec. 18, 2003

(87) PCT Pub. No.: WO02/066416

PCT Pub. Date: Aug. 29, 2002

(65) Prior Publication Data

US 2004/0106830 A1  Jun. 3, 2004

(30) Foreign Application Priority Data

Feb. 21, 2001 (JP) ............... 2001-045430
Oct. 5, 2001 (JP) ............... 2001-309322

(51) Int. Cl.
*C07D 491/052* (2006.01)
(52) U.S. Cl. ..................................... 546/92
(58) Field of Classification Search .................. None
See application file for complete search history.

(56) References Cited

U.S. PATENT DOCUMENTS 5,391,745 A * 2/1995 Danishefsky et al. ......... 546/48

FOREIGN PATENT DOCUMENTS

EP          845464 A2      6/1998
WO     WO 94/11376 A1    5/1994

OTHER PUBLICATIONS

Curran, Dennis P. et al., "Cascade Radical Reactions of Isonitriles: A Second-Generation Synthesis of (20S)-Camptothecin, Topotecan, Irinotechan, and GI-147211C**," Angew. Chem. Int. Ed. Engl. 1995, 34, 2683-2684.
Josien, Hubert et al., "A General Synthetic Approach to the (20S)-Camptothecin Family of Antitumor Agents by a Regiocontrolled Cascade Radical Cyclization of Aryl Isonitriles," Chemistry a European Journal, 1998, vol. 4, No. 1, pp. 67 to 83.
Gann to Kagaku Ryohou 17, p. 115-120, 1990 with an abridged English translation; p. 116, right column lines 9 from the bottom to last line.
She, Wang, et al., "Concise Total Syntheses of dl-Camptothecin and Related Anticancer Drugs," J. Org. Chem. 1993, 58, 611-617.
Henegar, Kevin E., et al., "Practical Asymmetric Synthesis of (S)-4-Ethyl-7,8-dihydro-4-hydroxy-1H-pyranol[3,4-f]indolizine-3,6,10(4H)-trione, a Key Intermediate for the Synthesis of Irinotecan and Other Camptothecin Analogs," J. Org. Chem., 1997, vol. 62, No. 19, pp. 6588 to 6597.
Sawada, Seigo, et al., "Synthesis and Antitumor Activity of 20(S)-Camptothecin Derivatives: Carbamate-Linked, Water-Soluble Derivatives of 7-Ethyl-10-hydroxycamptothecin," T. Chem. Pharm. Bull. 1991, 39, 1446.

* cited by examiner

*Primary Examiner*—Brian J. Davis
(74) *Attorney, Agent, or Firm*—Wolf, Greenfield & Sacks, P.C.

(57) ABSTRACT

The present invention is to prepare efficiently 2'-amino-5'-hydroxypropiophenone corresponding to the AB-ring part of camptothecin (CPT) skeleton and a tricyclic ketone corresponding to the CDE-ring part in order to provide efficiently CPT by the total synthesis, which is a starting material for irinotecan hydrochloride and various kinds of camptothecin derivatives, and to provide stably CPT and its derivatives.

27 Claims, No Drawings

METHOD OF SYNTHESIZING CAMPTOTHECIN-RELATING COMPOUNDS

RELATED APPLICATIONS

This application is a national stage filing under 35 U.S.C. § 371 of PCT International application PCT/JP02/01538, filed Feb. 21, 2002.

TECHNICAL FIELD

The present invention relates to a process for synthesizing camptothecin related compound(s). More particularly, the invention relates to a process for preparing intermediates related to the synthesis of camptothecin analogs having an anti-tumor activity and use of said intermediates, and relates to a total synthesis of camptothecin analogs.

BACKGROUND ART

Camptothecin (hereinafter described as CPT) isolated from the bark, root, fruit, leaf and the like of *Camtotheca acuminata* of Chinese origin is a pentacyclic alkaloid and is known to show the anti-tumor activity by inhibition of a nucleic acid synthesis. In the meantime, as to a camptothecin derivative the induction of diarrhea and the like as a side effect are reported (Gann to Kagaku Ryohou 17, p 115–120, 1990), leaving a problem to cause disorder for the gastrointestinal tract, and therefore, various kinds of derivatives have been examined to reduce the toxicity, to increase the effect, and so on.

Thus, the inventors already reported 7-ethyl-10-[4-(1-piperidino)-1-piperidino]carbonyloxycamptothecin.hydrochloride.trihydrate (hereinafter described as CPT-11), the water soluble semisynthetic derivative of CPT, as a compound which is reduce in toxicity compared to CPT, and it is at present widely used as the anti-tumor agent (general name; irinotecan hydrochloride).

Camptothecin analogs such as CPT-11 can be derived by a chemical modification of CPT obtained from natural materials.

However, owing to an extremely low amount of CPT obtained from natural materials such as *Camtotheca acuminata* which is the starting material, it is anticipated that according to an increased demand of CPT-11 which is a useful derivative and the like, a sufficient supply of CPT becomes difficult notwithstanding a measure for the starting material supply such as afforestation. Although the total synthesis is also examined, it is the present situation that it has not yet been into practical use.

As a process by total synthesis is known the method of Shen, W. et al. represented by the below reaction scheme via Friedländer reaction of the aminopropiophenone and the tricyclic ketone (J. Org. Chem. 1993, 58, 611–617 "Concise Total Syntheses of dl-Camptothecin and Related Anticancer Drugs.", though there are problems that the steps are tedious, the yields are not sufficient and only the racememate is synthesized.

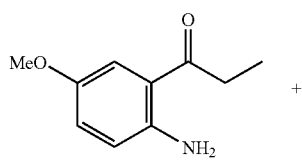

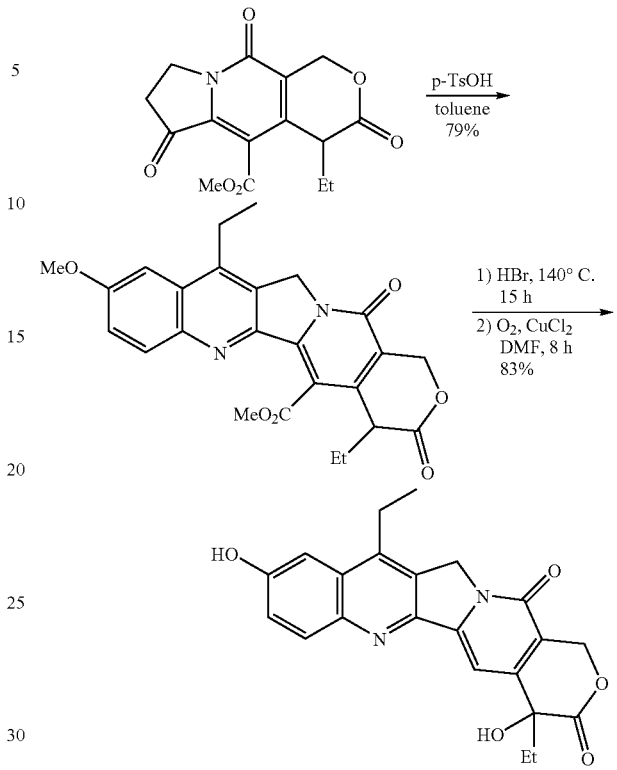

In the meantime, although Curran, D. P. et al. carried out a total synthesis by the method using a cascade radical cyclization of the aryl isonitrile and the iodopyridone represented by the below reaction scheme (Chem. Eur. J. 1998, 4, 67–83 "A General Synthetic Approach to the (20S)-Camptothecin Family of Antitumor Agents by a Regiocontrolled Cascade Radical Cyclization of Aryl Isonitriles."), problems are pointed out in which the yield of the cyclization reaction is not sufficient and deprotection of the protective group is necessary after cyclization.

-continued

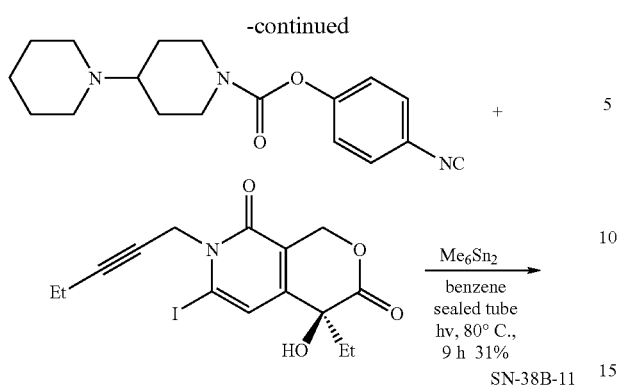

Additionally, although the above Curran, D. P. et al. synthesized 4-iodo-2-methoxy-6-trimethylsilylpyridine-3-carbaldehyde, an intermediate in the synthesis of the tricyclic ketone part of CPT analogs, according to the below scheme,

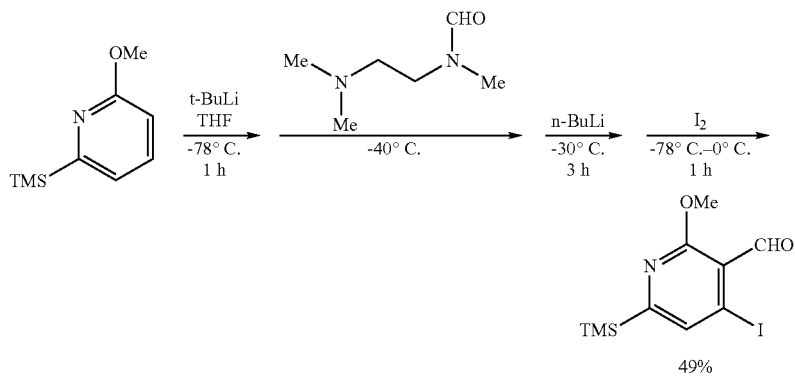

Josien, H; Ko, S.-B; Bom, D; Curran, D.P. Chem Br. J. 1988, 4, NO 1, 67.

this method is highly dangerous due to the necessity to use t-BuLi easily flammable in a large amount industrially, and the reaction at −78° C. as a reaction temperature is required, making it impossible to enlarge the batch size. Further, owing to the necessity of a complicated temperature control in the total reaction system it was not an industrially practical reaction system.

DISCLOSURE OF INVENTION

It is an object of the invention to provide efficiently CPT, which is a starting material for irinotecan hydrochloride and various kinds of camptothecin derivatives, and camptothecin analogs such as 7-ethyl-10-hydroxycamptothecin, which is a key intermediate of the irinotecan hydrochloride synthesis, by a practical total synthesis. Particularly, it is an object of the invention to synthesize an intermediate corresponding to the AB-ring part of camptothecin skeleton and an intermediate corresponding to the CDE-ring part respectively, and further to synthesize camptothecin analogs using these intermediates.

MODE FOR CARRYING OUT THE INVENTION

In view of these circumstances the inventors made an extensive research, and consequently as to the AB-ring part, made Compound (a) (5-hydroxy-2-nitrobenzaldehyde):

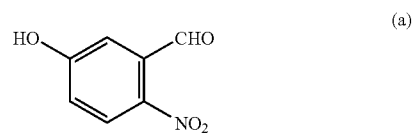

(a)

a starting material, and found a means to provide CPT and its derivatives stably by an efficient preparation of 2'-amino-5'-hydroxypropiophenone corresponding to the AB-ring part of CPT skeleton, and as to the CDE-ring part starting from Compound (k) (2-methoxy-6-trimethylsilylpyridine (MTP)):

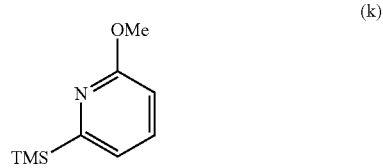

(k)

(wherein TMS represents a trimethylsilyl group, and Me represents a methyl group.)

found a means to provide CPT and its derivatives stably by an efficient preparation of a tricyclic ketone corresponding to the CDE-ring part of CPT skeleton, and established a total synthetic process for CPT analogs by an appropriate combination of these means without using natural materials, finishing the invention.

Namely, the invention relates to a process for preparing 2'-amino-5'-hydroxypropiophenone corresponding to the AB-ring of CPT skeleton according to the route;

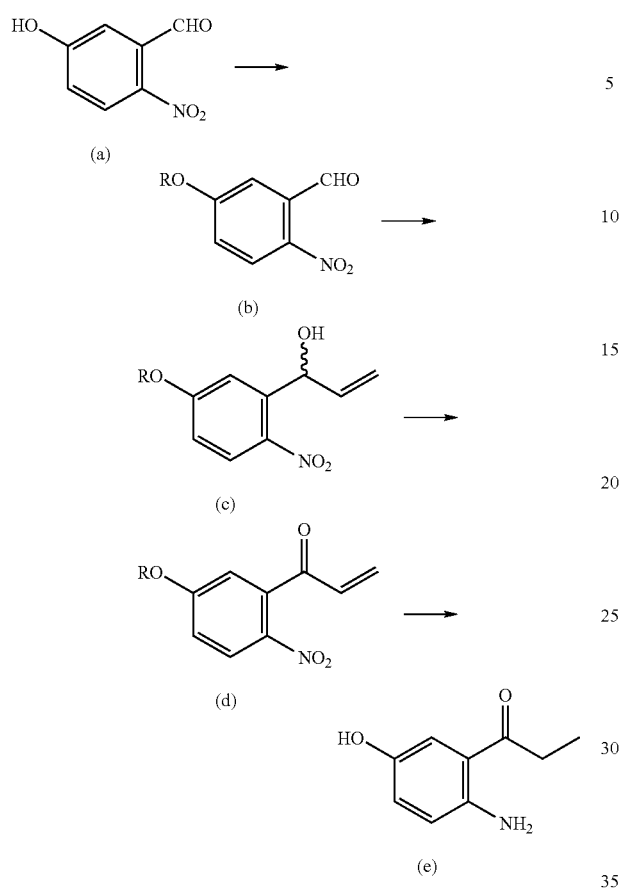

(a), (b), (c), (d), (e)

(wherein R represents a protective group.), and relates to a total synthetic process of CPT analogs by the appropriate combination of a process for the tricyclic ketone corresponding to the CDE-ring part of CPT skeleton comprising particularly synthesis of 3-formyl-4-iodo-2-methoxy-6-trimethylsilylpyridine (Compound (l)) from 2-methoxy-6-trimethylsilylpyridine (Compound (k)) or 3-hydroxymethyl-4-iodo-2-methoxy-6-trimethylsilylpyridine (Compound (v)) by improving and optimizing a process according to the synthetic route;

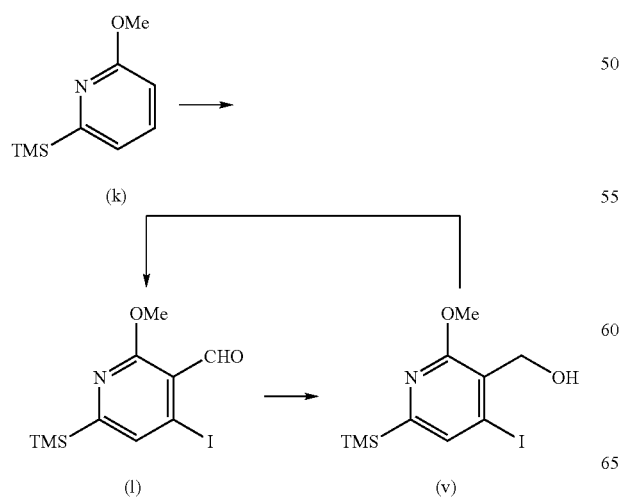

(k), (l), (v)

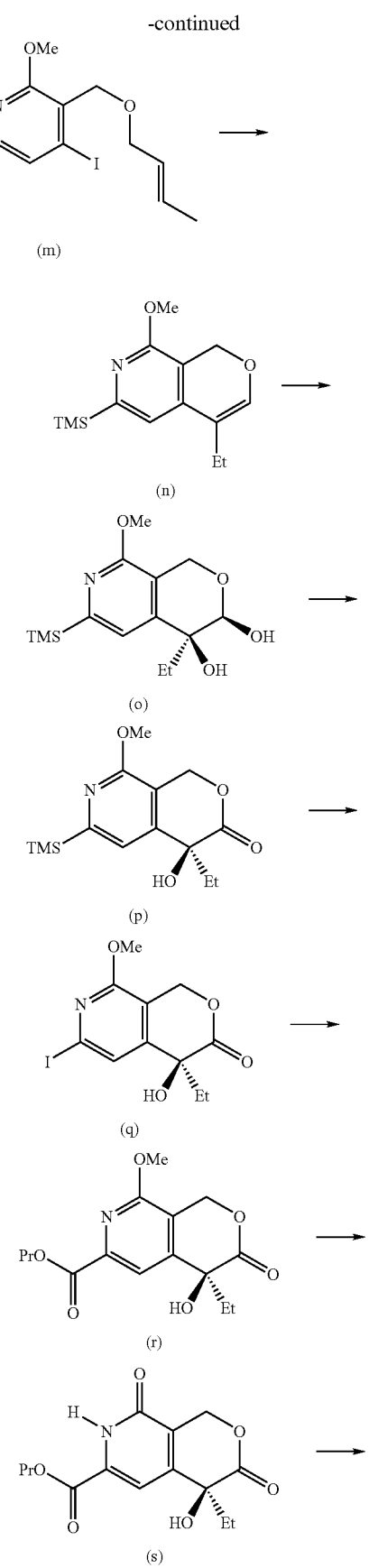

(m), (n), (o), (p), (q), (r), (s)

-continued

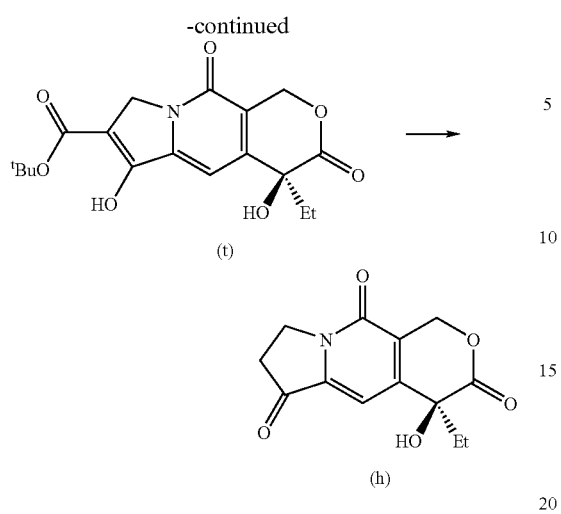

(wherein TMS is a trimethylsilyl group, Me is a methyl group, Et is an ethyl group, Pr is a propyl group, and $^t$Bu is a t-butyl group.), established on the basis of Curran route (Josien, H.; Ko, S. B.; Bom, D.: Curran, D. P. Chem. Eur. J. 1998, 4 67–83) and Pharmacia & Upjohn route (herein after described as P&U route; Heneger, K. E.; Ashford, S. W.; Baughman, T. A.; Sih, J. C.; Gu, R. L. J. Org. Chem. 1997, 62, 6588–6597.) which are synthetic routes currently known. Further, since Compound (v) is a byproduct arising in the process to synthesize 3-(2-butenyloxymethyl)-4-iodo-2-methoxy-6-trimethylsilylpyridine (Compound (m)), in the above synthetic route Compound (l) is described in the downstream.

Particularly, the invention relates to a process for preparing 2'-amino-5'-hydroxypropiophenone to synthesize camptothecin analogs, wherein from Compound (a):

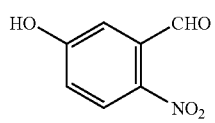

Compound (b):

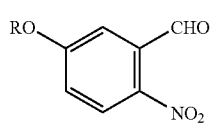

is produced; and from Compound (b) Compound (c):

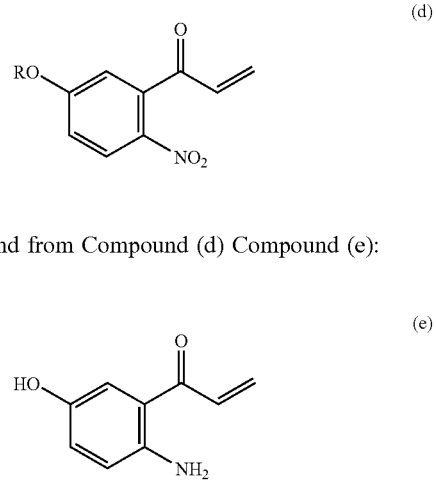

is produced; and from Compound (c) Compound (d):

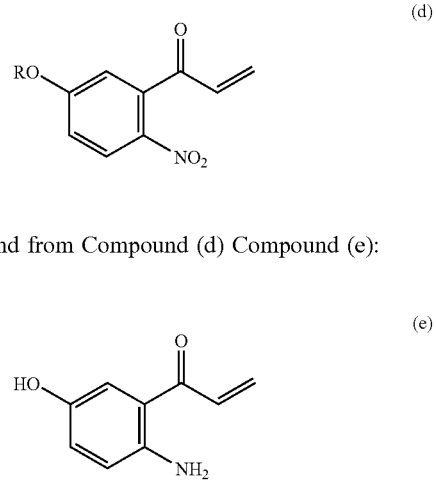

is produced; and from Compound (d) Compound (e):

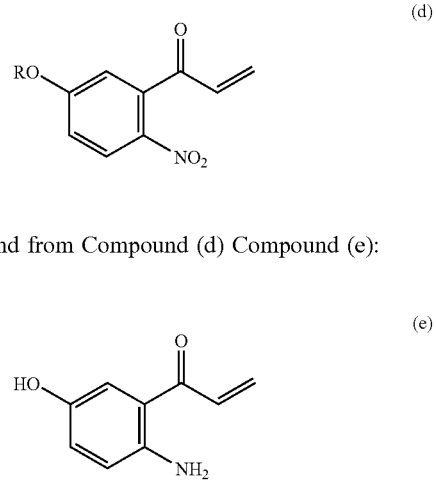

is produced; wherein R is a protective group which can be deprotected by a catalytic reduction.

Also, the invention relates to the above process, wherein the protective group which can be deprotected by a catalytic reduction is a benzyl group.

Further, the invention relates to the above process, wherein it contains one or more steps selected from the group consisting of (1) a step to obtain Compound (b) mixing Compound (a), a benzylation reagent and a base, and stirring said mixture in solvent under reflux;

(2) a step to obtain Compound (c) by dropping Grignard reagent to Compound (b) under an inert gas atmosphere;

(3) a step to obtain Compound (d) mixing Compound (c) and an oxidizing agent and stirring the mixture;

(4) a step to obtain Compound (e) by a catalytic reduction of Compound (d).

Further, the invention relates to the above process wherein in the step (1) the solvent is dimethylformamide.

The invention also relates to the above process wherein in the step (2) the Grignard reagent is vinyl magnesium bromide.

Further, the invention relates to the above process wherein in the step (3) the oxidizing agent is Jones reagent, manganese dioxide or TEMPO-(2,2,6,6-tetramethylpiperidine-1-oxyl)-sodium hypochlorite.

Also, the invention relates to compound represented by formula (c'):

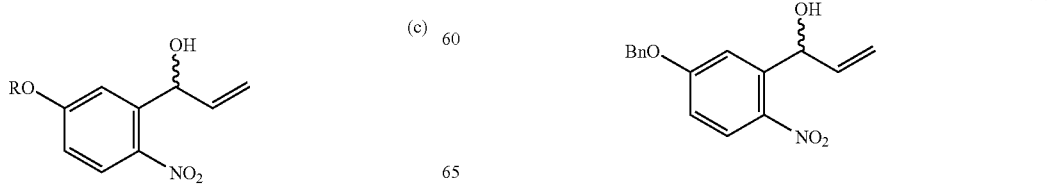

(wherein Bn is a benzyl group.).

Further, the invention relates to compound represented by formula (d'):

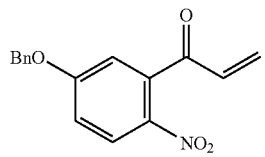
(d')

(wherein Bn is a benzyl group.).

Also, the invention is a process for preparing 2'-amino-5'-hydroxypropiophenone to synthesize camptothecin analogs, wherein from Compound (a):

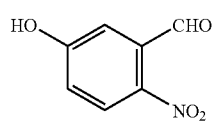
(a)

Compound (c''):

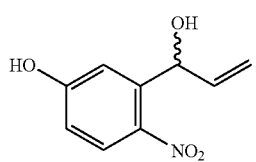
(c'')

is produced; and from Compound (c'') Compound (d''):

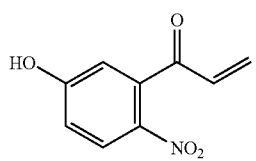
(d'')

is produced; and from Compound (d'') Compound (e):

(e)

is produced.

Further, the invention relates to the above process, wherein it contains one or more steps selected from the group consisting of
(1) a step to obtain Compound (c'') by dropping Grignard reagent to Compound (a) under an inert gas atmosphere;
(2) a step to obtain Compound (d'') mixing the Compound (c'') and an oxidizing agent and stirring the mixture; and
(3) a step to obtain Compound (e) by a catalytic reduction of Compound (d'').

The invention also relates to the above process wherein in the step (1) the Grignard reagent is vinyl magnesium bromide.

Further, the invention relates to the above process wherein in the step (2) the oxidizing agent is Jones reagent, manganese dioxide or TEMPO-sodium hypochlorite.

The invention also relates to use of 2'-amino-5'-hydroxypropiophenone, which is obtained by the above process, to the preparation of camptothecin analogs.

Further, the invention relates to a process for preparing camptothecin analogs, comprising reaction of 2'-amino-5'-hydroxypropiophenone obtained by the above process and a tricyclic ketone.

The invention also is a process for preparing the tricyclic ketone to synthesize camptothecin analogs, wherein from Compound (k):

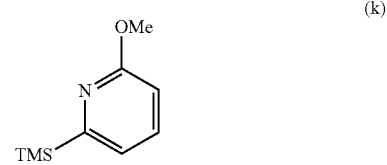
(k)

(wherein TMS is a trimethylsilyl group, and Me is a methyl group.), or Compound (v):

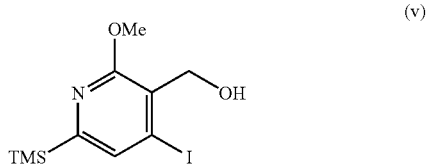
(v)

(wherein TMS is a trimethylsilyl group, and Me is a methyl group.)

Compound (l):

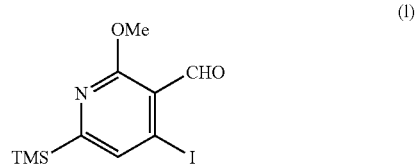
(l)

(wherein TMS is a trimethylsilyl group, and Me is a methyl group.)

is produced; and from Compound (l) Compound (m):

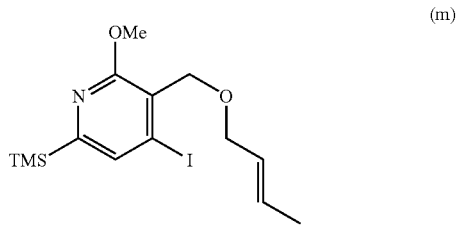
(m)

(wherein TMS is a trimethylsilyl group, and Me is a methyl group.)

is produced; and from Compound (m) Compound (n):

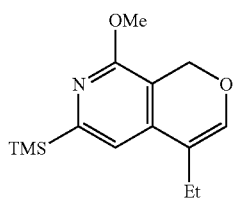

(wherein TMS is a trimethylsilyl group, Me is a methyl group, and Et is an ethyl group.)

is produced; and from Compound (n) Compound (o):

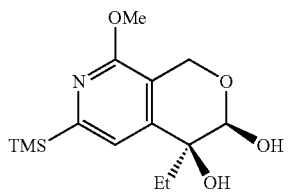

(wherein TMS is a trimethylsilyl group, Me is a methyl group, and Et is an ethyl group.)

is produced; and from Compound (o) Compound (p):

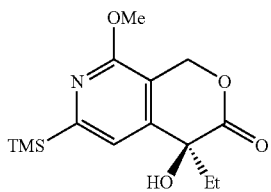

(wherein TMS is a trimethylsilyl group, Me is a methyl group, and Et is an ethyl group.)

is produced; and from Compound (p) Compound (q):

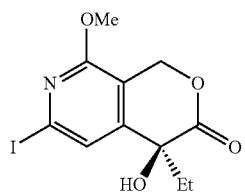

(wherein Me is a methyl group, and Et is a ethyl group.)

is produced; and from Compound (q) Compound (r):

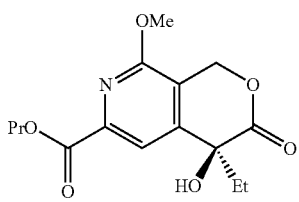

(wherein Me is a methyl group, Et is an ethyl group, and Pr is a propyl group.)

is produced; and from Compound (r) Compound (s):

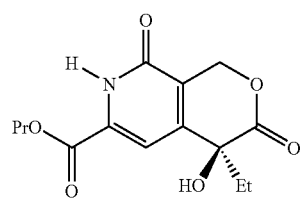

(wherein Et is an ethyl group, and Pr is a propyl group.)

is produced; and from Compound (s) Compound (t):

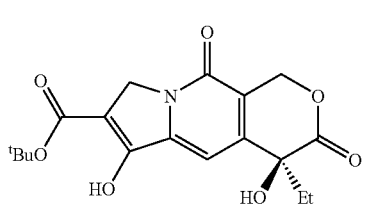

(wherein Et is an ethyl group, and tBu is a t-butyl group.)

is produced; and from Compound (t) Compound (h):

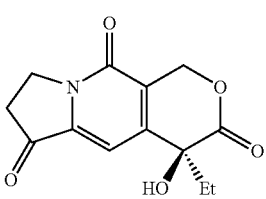

(wherein Et is an ethyl group.)

is produced; and wherein it contains one or more steps selected from the group consisting of;

(1) a step to obtain Compound (l) mixing Compound (k), a lithiating agent, a formylation reagent and an iodination reagent;

(2) a step to obtain Compound (m) mixing Compound (l), crotyl alcohol, triethylsilane and an acid, and reacting said mixture without use of solvent;

(3) a step to obtain Compound (l) mixing Compound (v), a byproduct in the step (2), with an oxidizing agent and a base;

(4) a step to obtain Compound (n) mixing Compound (m), a palladium catalyst, a base and a phase-transfer catalyst, and refluxing said mixture in solvent;

(5) a step to obtain Compound (o) mixing Compound (n), an osmium catalyst, a co-oxidizing agent, a base and an asymmetric reagent;

(6) a step to obtain Compound (p) mixing Compound (o), a base and iodine, and refluxing said mixture in an alcohol-water mix liquid;

(7) a step to obtain Compound (q) mixing Compound (p) and a desilylation-iodination reagent;

(8) a step to obtain Compound (r) mixing Compound (q), a palladium catalyst and a base, and reacting said mixture in 1-propanol under a carbon monoxide gas atmosphere;

(9) a step to obtain Compound (s) mixing Compound (r) and a demethylation reagent, and reacting said mixture at room temperature;

(10) a step to obtain Compound (t) reacting Compound (s) under the presence of t-butyl acrylate and a base.

Further, the invention relates to the above process wherein in the step (1) the lithiating agent is n-butyl lithium.

The invention also relates to the above process wherein in the step (1) the reaction temperature is the constant temperature of −30 to −40° C.

Further, the invention relates to the above process wherein in the step (3) the oxidizing agent is TEMPO-sodium hypochlorite.

The invention also relates to the above process wherein in the step (4) the base is potassium carbonate or N,N-diisopropylethylamine.

Further, the invention relates to the above process wherein in the step (4) the solvent is tetrahydrofuran, or a diisopropyl ether-acetonitrile-water mix liquid.

The invention also relates to the above process wherein in the step (5) the osmium catalyst is potassium osmate(VI).

Further, the invention relates to the above process wherein in step (6) the iodine against Compound (o) is in 4 equivalent.

The invention also relates to the above process wherein in the step (7) the desilylation-iodination reagent is iodine-silver trifluoroacetate or N-chlorosuccinimide-sodium iodide.

Further, the invention relates to the above process, wherein Compound (q) is purified chemically by purification steps comprising a step to add the reaction product obtained by the step to produce Compound (q) from Compound (p) to an aqueous alkaline solution and to stir; a step to add an organic solvent and to stir, followed by removal of the organic layer; and a step to make the aqueous layer acidic and to extract with an organic solvent.

The invention also relates to the above process wherein the aqueous alkaline solution is an aqueous sodium hydroxide solution.

Further, the invention relates to the above process wherein the organic solvent is chloroform.

The invention also relates to the above process, wherein Compound (q) is purified optically by purification steps comprising a step to dissolve the reaction product obtained by the step to produce Compound (q) from Compound (p) in a high polarity solvent, followed by lamination of a low polarity solvent; and a step to filter a precipitate which is followed by concentration of the filtrate to dryness under reduced pressure.

Further, the invention relates to the above process wherein the high polarity solvent is chloroform.

The invention also relates to the above process wherein the low polarity solvent is n-hexane.

Further, the invention relates to the above process wherein in step (10) the base is potassium carbonate.

The invention also relates to use of the tricyclic ketone obtained by the above process to the preparation of camptothecin analogs.

Further, the invention relates to the process for preparing camptothecin analogs wherein the tricyclic ketone obtained by the above process is reacted with 2'-amino-5'-hydroxypropiophenone.

The invention also relates to the above process, wherein the 2'-amino-5'-hydroxypropiophenone is 2'-amino-5'-hydroxypropiophenone obtained by the above process.

Further, the invention relates to the above process, wherein the tricyclic ketone and 2'-amino-5'-hydroxypropiophenone are mixed and said mixture is reacted under an inert atmosphere.

The invention makes it becoming possible to prepare efficiently 2'-amino-5'-hydroxypropiophenone corresponding to the AB-ring part of the CPT skeleton by adopting these constituents and makes it possible to put a total synthesis of CPT into practical use. Additionally, as to the intermediate Compound (c') and Compound (d') in the process of the invention there is yet no report of their synthesis, and therefore they are useful novel compounds.

The invention also makes it possible to carry out practically an asymmetric synthesis of compound(s) by adopting these constituents, whereby compound(s) have the skeleton becoming the CDE-ring part (the tricyclic ketone part) in the CPT skeleton.

As to the synthesis of 2'-amino-5'-hydroxypropiophenone of the AB-ring in the CPT skeleton, a process for preparing 2'-amino-5'-hydroxypropiophenone comprises one or more steps of the followings;

(1) the step to synthesize 5-benzyloxy-2-nitrobenzaldehyde (Compound (b')) from 5-hydroxy-2-nitrobenzaldehyde (Compound (a'));
(2) the step to synthesize 1-(5-benzyloxy-2-nitrophenol)-2-propen-1-ol (Compound (c')) from Compound (b');
(3) the step to synthesize 1-(5-benzyloxy-2-nitrophenol)-2-propen-1-one (Compound (d')) from Compound (c'); and
(4) the step to synthesize 2'-amino-5'-hydroxypropiophenone (Compound (e')) from Compound (d').

As a typical synthetic route, the following synthetic route:

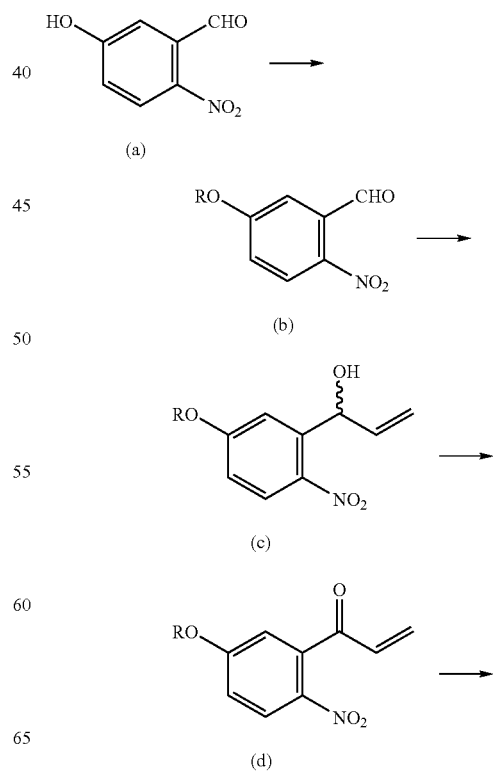

-continued

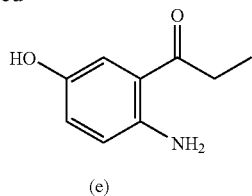

(e)

(wherein R is a protective group which can be deprotected by a catalytic reduction)

is shown.

In the invention, in case R is a protective group which can be deprotected by a catalytic reduction, it is not particularly limited, but typical examples are benzyl ether type protective groups such as a benzyl, methoxybenzyl, 2,6-dimethylbenzyl or 4-nitrobenzyl groups, and benzyl carbonate type protective groups such as a benzyloxycarbonyl group, though a benzyl group is expediently used particularly in view of a reagent cost.

Further, as to Compound (a) which is the starting material, that synthesized by a known method, that chemically converted from a similar compound, that isolated and purified from various kinds of natural materials, and natural materials containing Compound (a) can be used. A commercially available reagent may also be used.

In the following the above steps (1) to (4) are explained more specifically.

In the step (1), Compound (a) is dissolved or suspended in solvent, followed by addition of a benzylation reagent and a base and by heating under stirring to afford Compound (b).

As solvent N,N-dimethylformamide (DMF), dimethyl sulfoxide, chloroform, acetonitrile, ethanol, water and the like can be used, and DMF is preferable particularly in view of solubility and reactivity.

The used amount of DMF may be three or more times based on that of Compound (a), preferably in the range of 3 to 20 times.

As a benzylation reagent any one can expediently be used if it is conventionally used. Illustrative of specific examples are benzyl chloride, benzyl bromide, benzyl iodide, phenyldiazomethane, dibenzyl carbonate and the like, and in particular benzyl chloride can expediently be used.

The used amount of a benzylation reagent may appropriately be prepared according to the reagent, though in case of using, for example, benzyl chloride, it is used in 1 to 5 equivalent based on that of Compound (a), preferably 1 to 2 equivalent.

As a base any one can expediently be used if it is conventionally used. Illustrative of specific examples are potassium carbonate, sodium carbonate, cesium carbonate, sodium hydroxide, potassium hydroxide and the like, and in particular potassium carbonate can expediently be used.

The used amount of a base may appropriately be prepared according to the reagent, though in case of using, for example, potassium carbonate, it is used in 1 to 10 equivalent based on that of Compound (a), preferably 1 to 4 equivalent.

As a heating temperature it is in the range of 60 to 100° C., preferably 60 to 80° C.

Additionally, the reaction time is in the range of 0.5 to 24 hours, preferably 1 to 20 hours.

In the step (2), Compound (c) is obtained dropping Grignard reagent to Compound (b) under an inert gas atmosphere.

As an inert gas any one may be used in case it is a noble gas such as argon, helium, neon, krypton, xenon, radon or the like, or a gas of low reactivity such as nitrogen, and argon and nitrogen are preferable particularly in view of the cost.

As Grignard reagent any one can expediently be used if it is conventionally used. Illustrative of specific examples are vinyl magnesium bromide, vinyl magnesium chloride, vinyl magnesium iodide and the like, and in particular vinyl magnesium bromide can expediently be used.

The used amount of Grignard reagent may be prepared according to the reagent, though in case of, for example, vinyl magnesium bromide, it is used in 1 to 2 equivalent based on that of Compound (b), preferably 1 to 1.5 equivalent.

In case Grignard reagent is dropped to Compound (b) solution or on the contrary Compound (b) solution is dropped to Grignard reagent, synthesis of Compound (c) is possible, though in order to reduce the production of the reduced type byproduct (hereinafter described as Compound (f))

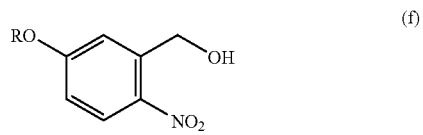

(f)

(wherein R is a protective group which can be deprotected by a catalytic reduction.), it is preferable to drop Grignard reagent to Compound (b) solution.

As a used amount of solvent in the reaction, for example, tetrahydrofuran (hereinafter referred to as THF) may be in an amount of 10 to 100 times, and to reduce particularly production of the alcohol an amount of 50 to 100 times is preferable.

Also, the reaction temperature is preferably not more than 10° C., and to reduce particularly production of the alcohol −78 to −40° C. is preferable.

Additionally, the reaction period is 0.1 to 3 hours, and in particular, preferably, it is 0.5 to 1 hours.

In the step (3), Compound (d) can be obtained mixing Compound (c) with an oxidizing agent and stirring the mixture.

As an oxidizing agent any one can expediently be used if it is conventionally used. Illustrative of such oxidizing agents are, for example, manganese dioxide, Dess-Martin Periodinane, Jones reagent ($Na_2Cr_2O_7/H_2SO_4$), PCC, PDC, DMSO/oxalyl chloride/triethylamine (Swern oxidation), TEMPO-sodium hypochlorite and the like, and in particular, manganese dioxide, Dess-Martin Periodinane, Jones reagent and TEMPO-sodium hypochlorite can preferably be used.

As to these oxidizing agents, one prepared just before use is preferably used, and in case of, for example, manganese dioxide, one prepared just before use from potassium permanganate and manganese sulfate can expediently be used.

The used amount of an oxidizing agent may appropriately be prepared according to the reagent, though in case of, for example, manganese dioxide, it is used in 2 to 50 times based on that of Compound (c), preferably 4 to 10 times.

As solvent, for example, chloroform, methylene chloride, ethyl acetate, benzene, toluene and the like can expediently be used, and in particular, chloroform and methylene chloride are preferable.

The used amount of solvent is 5 to 50 times, preferably 10 to 20 times.

Further, the reaction time is 1 to 48 hours and in particular, 1 to 18 hours are preferable.

In the step (4), Compound (e) can be obtained by a catalytic reduction of Compound (d).

As a catalyst for reduction palladium-carbon, palladium hydroxide-carbon, rhodium-alumina and the like can expediently be used, and in particular, palladium-carbon and palladium hydroxide-carbon are preferable.

The used amount of a catalyst for reduction is 0.01 to 0.5 equivalent based on that of Compound (d), preferably 0.05 to 0.2 equivalent.

As solvent any one can expediently be used if it is conventionally used, though ethyl acetate is preferable in view of solubility.

The used amount of solvent is 5 to 50 times, preferably 10 to 20 times.

Additionally, the reaction time is 0.1 to 24 hours and in particular, preferably, it is 1 to 3 hours.

Further, instead of synthesizing Compound (e) via the above steps (1) to (4), from Compound (a):

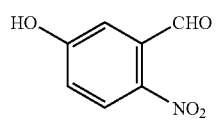

(a)

Compound (c″):

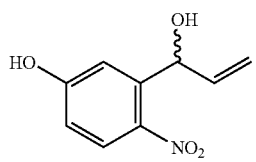

(c″)

is produced; and from Compound (c″) Compound (d″):

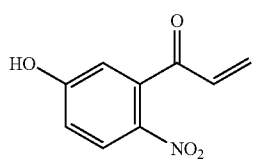

(d″)

is produced; and from Compound (d″) Compound (e):

(e)

can be produced. In this synthetic route, Compound (c″) can be obtained dropping Grignard reagent to Compound (a) under an inert atmosphere. Further, Compound (d″) can be obtained mixing Compound (c″) and an oxidizing agent and stirring the mixture, and Compound (e) can be obtained by a catalytic reduction of Compound (d″). Here, Grignard reagent and the oxidizing agent which can be used are the same as those in the above steps (2) and (3). In this synthetic route, since no protecting group is used, the synthesis of the AB-ring part can simply be carried out.

Further, camptothecin analogs can be prepared by reacting Compound (e) obtained in the step (4) or the synthetic route described previously and a tricyclic ketone, though as tricyclic ketone like this, for example, Compound (h):

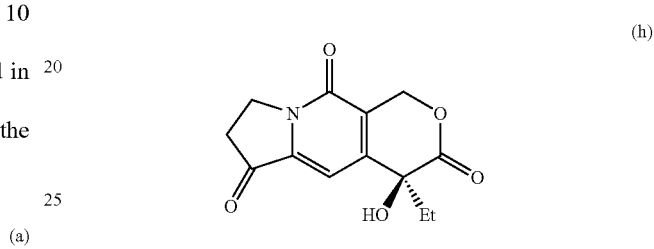

(h)

can be used.

As to synthesis of the CDE-ring part (the tricyclic ketone part) of the CPT skeleton, preparation of the tricyclic ketone is carried out via the following synthetic route.

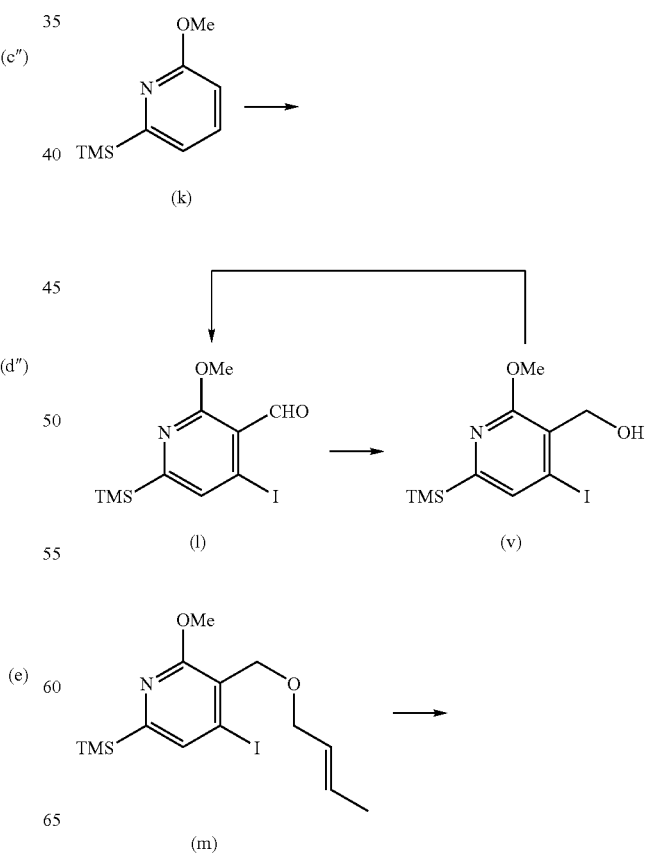

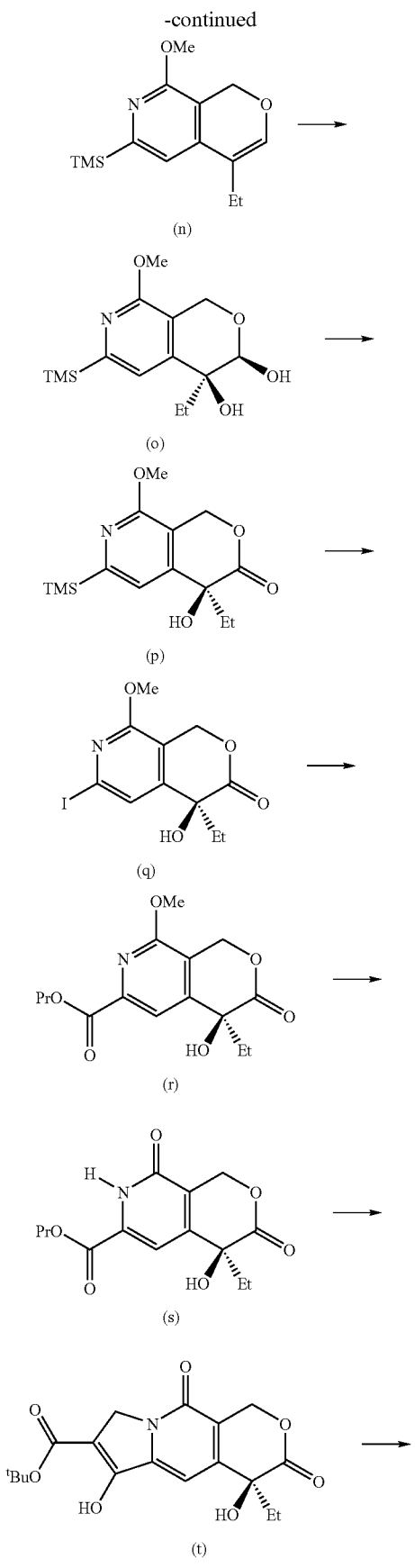

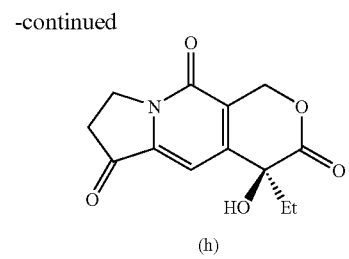

(wherein TMS is a trimethylsilyl group, Me is a methyl group, Et is an ethyl group, Pr is a propyl group, and ′Bu is a t-butyl group.)

As to the starting Compound (k) in the above synthetic route, that synthesized by the above Curran route (Josien, H,; Ko, S. B.; Bom, D.: Curran, D. P. Chem. Eur. J. 1998, 4 67–83) described previously, that chemically converted from a similar compound that isolated and purified from various kinds of natural materials, or a natural material itself, which contains Compound (k), can be used.

A preferable synthetic process for synthesizing the tricyclic ketone in the above synthetic route contains one or more steps from the 12 steps consisting of;

(1) in the step to synthesize 4-iodo-2-methoxy-6-trimethylsilyl-3-pyridinecarbaldehyde (hereinafter referred to as Compound (l)) from 2-methoxy-6-trimethylsilylpyridine (hereinafter referred to as Compound (k)), n-butyl lithium is used as a base and the reaction is carried out at the constant temperature of to −40° C.;

(2) in the step to synthesize 3-(2-butenyloxymethyl)-4-iodo-2-methoxy-6-trimethylsilylpyridine (hereinafter referred to as Compound (m)) from Compound (l), a reaction solvent is not used;

(3) in the step to synthesize Compound (l) from 3-hydroxymethyl-4-iodo-2-methoxy-6-trimethylsilylpyridine (hereinafter referred to as Compound (v)), TEMPO-sodium hypochlorite is used as an oxidizing agent;

(4) in the step to synthesize 4-ethyl-8-methoxy-6-trimethylsilyl-1H-pyrano[3,4-c]pyridine (hereinafter referred to as Compound (n)) from Compound (m), a mixed liquid of diisopropyl ether, acetonitrile and water is used as a reaction solvent, and N,N-diisopropylethylamine is used as a base;

(5) in the step to synthesize (S)-4-ethyl-3,4-dihydro-3,4-dihydroxy-8-methoxy-6-trimethylsilyl-1H-pyrano[3,4-c]pyridine (hereinafter referred to as Compound (o)) from Compound (n), potassium osmate (VI) is used as an osmium catalyst;

(6) in the step to synthesize (S)-4-ethyl-3,4-dihydro-4-hydroxy-8-methoxy-6-trimethylsilyl-3-oxo-1H-pyrano[3,4-c]pyridine (hereinafter referred to as Compound (p)) from Compound (o), the reaction mixture is refluxed using iodine (4 equivalent);

(7) in the step to synthesize (S)-4-ethyl-3,4-dihydro-4-hydroxy-6-iodo-8-methoxy-3-oxo-1H-pyrano[3,4-c]pyridine (hereinafter referred to as Compound (q)) from Compound (p), N-chlorosuccinimide-sodium iodide is used in acetic acid;

(8) in the step to purify Compound (q) chemically, the mixture is added with a basic solution such as aqueous sodium hydroxide solution to make a solution alkaline, washed with an organic solvent such as chloroform, and then the water layer after acidification is extracted with an organic solvent such as chloroform;

(9) in the step to purify Compound (q) optically, Compound (q) is dissolved in a high polarity solvent such as chloroform and laminated with a low polarity solvent such as n-hexane to give precipitate which is removed by filtration, followed by concentration of the filtrate;

(10) in the step to synthesize propyl (S)-4-ethyl-3,4-dihydro-4-hydroxy-8-methoxy-3-oxo-1H-pyrano[3,4-c]pyridine-6-carboxylate (hereinafter referred to as Compound (r)) from Compound (q), palladium acetate is used as a palladium catalyst;

(11) in the step to synthesize propyl (S)-4-ethyl-3,4,7,8-tetrahydro-4-hydroxy-3,8-dioxo-1H-pyrano[3,4-c]pyridine-6-carboxylate (hereinafter referred to as Compound (s)) from Compound (r), the reaction is carried out at room temperature;

(12) in the step to synthesize 1,1-dimethylethyl (S)-4-ethyl-3,4,8,10-tetrahydro-4,6-dihydroxy-3,10-dioxo-1H-pyrano[3,4-f]indolidin-7-carboxylate (hereinafter referred to as Compound (t)) from Compound (s), Michel addition is carried out using potassium carbonate.

Further, (13) in the step to obtain SN-38 from (S)-4-ethyl-7,8-dihydro-4-hydroxy-1H-pyrano[3,4-f]indolidin-3,6,10 (4H)-trione (hereinafter referred to as Compound (h)) and Compound (e), SN-38 can be expediently be obtained carrying out the reaction in an inert gas atmosphere to afford SN-38 expediently.

In the following, the above 13 steps are explained more specifically.

In the step of (1), Compound (k) is dissolved in solvent, followed by addition of a litiation, formylation and iodination reagents and stirring to afford Compound (l).

As solvent tetrahydrofuran (THF), diethyl ether, hexane, heptane and the like can be used, and THF is preferable particularly in view of solubility and reactivity.

As a litiation reagent any one can expediently be used if it is conventionally used. Illustrative of specific examples are n-butyllithium, s-butyllithium, t-butyllithium, lithium diisopropylamide (LDA), lithium bis(trimethylsilyl)amide (LiHMDS) and the like, and n-butyllithium can expediently be used particularly in view of handling and reactivity.

The used amount of a litiation reagent may appropriately be prepared according to the reagent, though in case of using, for example, n-butyllithium, it is used in 2 to 10 equivalent based on that of Compound (k), preferably 2 to 5 equivalent.

Illustrative of specific examples of a formylation reagent are N-formyl-N,N',N'-trimethylethylenediamine, dimethylformamide (DMF) and the like, and N-formyl-N,N',N'-trimethylethylenediamine is expediently used considering the subsequent iodination.

The used amount of a formylation reagent, for example, in case of using N-formyl-N,N',N'-trimethylethylenediamine is used in 1 to 10 equivalent based on that of Compound (k), preferably 1 to 3 equivalent.

As an iodination reagent iodine, N-iodosuccinimide (NIS) and the like can be used, and iodine is preferable particularly in view of the cost and reactivity.

The used amount of an iodination reagent is used in 1 to 10 equivalent based on that of Compound (k), preferably 1 to 5 equivalent.

The reaction temperature is in the range of 0 to −78° C., preferably the constant temperature of −30 to −40° C.

In the step of (2), Compound (l) is added with crotyl alcohol, triethylsilane and an acid and stirred without using solvent to afford Compound (m).

As the used amount of crotyl alcohol, it is used in 1 to 10 equivalent based on that of Compound (k), preferably 2 to 5 equivalent.

As the used amount of triethylsilane, it is used in 1 to 10 equivalent based on that of Compound (k), preferably 1 to 4 equivalent.

As an acid trifluoroacetic acid (TFA), sulfuric acid, methanesulfonic acid, hydrochloric acid and the like can be used, and TFA is preferable particularly in view of reactivity.

The used amount of an acid, for example, in case of TFA is 1 to 15 equivalent based on that of Compound (l), preferably 5 to 10 equivalent.

In the step of (3), Compound (l) can be obtained by dissolving Compound (v), a by product in the step of (2), insolvent, followed by addition of an oxidizing agent and a base, and stirring.

As solvent any one can expediently be used if it is conventionally used. Illustrative of such solvent are dichloromethane, chloroform, actonitrile, toluene, n-hexane and the like, and toluene and n-hexane are preferable particularly in view of reactivity.

Illustrative of oxidizing agents are manganese dioxide, Dess-Martin Periodinane, Jones reagent ($Na_2Cr_2O_7/H_2SO_4$), PCC, PDC, DMSO-oxalyl chloride-triethylamine (Swern oxidation), TEMPO-hypochlorite and the like, and in particular, TEMPO-hypochlorite is preferable, more preferably TEMPO-sodium hypochlorite.

As the used amount of an oxidizing agent, for example, in case of TEMPO-sodium hypochlorite, TEMPO is used in 0.001 to 0.1 equivalent based on that of Compound (v), preferably 0.005 to 0.02 equivalent. Additionally, sodium hypochlorite is used in 1 to 5 equivalent, preferably 1 to 2 equivalent.

As a base any one can expediently be used if it is conventionally used. Illustrative of such bases are sodium bicarbonate, sodium carbonate, potassium carbonate, calcium carbonate, sodium hydroxide, calcium hydroxide, triethylamine and the like, with sodium bicarbonate being particularly preferable.

As the used amount of a base, for example, in case of sodium bicarbonate, it is used in 1 to 10 equivalent based on that of Compound (v), preferably 2 to 4 equivalent.

The reaction temperature is in the range of −10 to 30° C., preferably not −10 to 10° C. particularly to suppress a side reaction.

Additionally, the reaction period is in the range of 0.5 to 10 hours, preferably 0.5 to 5 hours.

In the step of (4), Compound (m) is dissolved in solvent, added with a palladium catalyst, a base and a phase-transfer catalyst, and refluxed to afford Compound (n).

As solvent acetonitrile, tertrahydrofuran (THF), diisopropyl ether (IPE), diethyl ether, toluene, water and the like can be used, and acetonitrile, THF, IPE and water are preferable particularly in view of reactivity, more preferably THF or an acetonitrile-IPE-water mix liquid.

As a palladium catalyst palladium acetate, tetrakis-(triphenylphosphine)palladium, dichlorobis-(triphenylphosphine)palladium, palladium chloride and the like can expediently be used, and palladium acetate is preferable particularly in view of reactivity.

The used amount of a palladium catalyst is in 0.01 to 1 equivalent based on that of Compound (m), preferably 0.05 to 0.2 equivalent.

As a base any one can expediently be used if it is conventionally used. Illustrative of such bases are, for example, sodium carbonate, potassium carbonate, calcium carbonate, cesium carbonate, triethylamine (TEA), N,N- diisopropylethylamine (DIPEA), sodium hydroxide, potassium hydroxide and the like, with potassium carbonate and DIPEA being particularly preferable.

The used amount of a base, for example, in case of DIPEA is in 1 to 20 equivalent based on that of Compound (m), preferably 5 to 10 equivalent.

As a phase-transfer catalyst any one can expediently be used if it is a quaternary ammonium salt or crown ether which are conventionally used, with tetrabutylammonium bromide being particularly preferable.

The used amount of a phase-transfer catalyst, for example, in case of tetrabutylammonium bromide is in 0.1 to 3 equivalent based on that of Compound (m), preferably 0.5 to 1.5 equivalent.

Further, the reaction period in case of using THF is in the range of 1 to 20 hours, preferably 4 to 10 hours. In case of using an acetonitrile-IPE-water mix liquid it is in the range of 0.5 to 10 hours, preferably 1 to 5 hours.

In the step of (5), Compound (n) is dissolved in an alcohol-water mix liquid, added with an osmium catalyst, a co-oxidizing agent, an asymmetric catalyst, a base and methanesulfonamide, and stirred to afford Compound (o).

Illustrative of alcohols are methanol, ethanol, 1-propanol, isopropanol (IPA), 1-butanol, 2-butanol, t-butyl alcohol and the like, and t-butyl alcohol is preferable particularly in view of reactivity.

As an osmium catalyst osmium tetraoxide, potassium osmate(VI) and the like can expediently be used, and potassium osmate(VI) is preferable particularly in view of handling. The used amount of an osmium catalyst is in 0.001 to 0.1 equivalent based on that of Compound (n), preferably 0.002 to 0.01 equivalent.

As a co-oxidizing agent potassium hexacyanoferrate(III), N-methymorpholine N-oxide (NMO) and the like can expediently be used, and potassium hexacyanoferrate(III) is preferable particularly in view of the reactivity.

The used amount of a co-oxidizing agent, for example, in case of potassium hexacyanoferrate(III), is used in 1 to 10 equivalent based on that of Compound (n), preferably 2 to 5 equivalent.

Illustrative of asymmetric catalysts are $(DHQD)_2PYR$, $(DHQD)_2PHAL$, $(DHQD)_2AQN$ and the like, and $(DHQD)_2PYR$ is preferable particularly in view of the optical yield.

The used amount of an asymmetric catalyst, for example, in case of $(DHQD)_2PYR$, is used in 0.005 to 0.1 equivalent based on that of Compound (n), preferably 0.01 to 0.05 equivalent.

As a base sodium carbonate, potassium carbonate, calcium carbonate, cesium carbonate, sodium hydroxide, potassium hydroxide and the like can be used, and potassium carbonate is preferable particularly in view of the reactivity.

The used amount of a base, for example, in case of potassium carbonate, is in 1 to 20 equivalent based on that of Compound (n), preferably 4 to 10 equivalent.

The used amount of methanesulfonamide is in 0.1 to 5 equivalent based on that of Compound (n), preferably 0.5 to 2 equivalent.

The reaction temperature is in the range of −10 to 30° C., preferably −10 to 10° C.

In the step of (6), Compound (o) is dissolved in solvent, added with a base and iodine, and refluxed to afford Compound (p).

Illustrative of solvent are methanol, ethanol, 1-propanol, isopropanol (IPA), water and the like, with a methanol-water mix liquid being particularly preferable in view of reactivity.

As a base any one can expediently be used if it is conventionally used. Illustrative of such bases are sodium carbonate, potassium carbonate, calcium carbonate, cesium carbonate, sodium hydroxide, potassium hydroxide and the like, with calcium carbonate being particularly preferable.

The used amount of a base, for example, in case of calcium carbonate, is in 1 to 10 equivalent based on that of Compound (o), preferably 2 to 5 equivalent.

The used amount of iodine is in 1 to 10 equivalent based on that of Compound (o), preferably 3 to 5 equivalent. Additionally, the reaction period is in the range of 0.5 to 20 hours, preferably 1 to 5 hours.

In the step of (7), Compound (p) is dissolved in solvent, and reacted under iodine-silver trifluoroacetate (hereinafter referred to as $I_2$—$CF_3COOAg$) or N-chlorosuccinimide-sodium iodide (hereinafter referred to as NCS—NaI) to afford Compound (q).

As to solvent, in case of $I_2$—$CF_3COOAg$ dichloromethane, carbon tetrachloride, chloroform and the like are expedient, and in particular, dichloromethane is preferable. Additionally, in case of NCS—NaI acetic acid, acetonitrile and the like can be used, and acetic acid is preferable particularly in view of reactivity.

As to the used amount of $I_2$—$CF_3COOAg$, $I_2$ is used in 1 to 10 equivalent based on that of Compound (p), preferably 2 to 4 equivalent. Additionally, $CF_3COOAg$ is used in 1 to 10 equivalent, preferably 2 to 4 equivalent.

As to the used amount of NCS—NaI, NCS is used in 1 to 20 equivalent based on that of Compound (p), preferably 5 to 8 equivalent. Additionally, NaI is used in 1 to 20 equivalent based on that of Compound (p), preferably 5 to 8 equivalent.

The reaction temperature in case of using $I_2$—$CF_3COOAg$ is 10 to 60° C., preferably 20 to 40° C. Further, in case of using NCS—NaI it is 20° C. to a reflux temperature, preferably 50 to 80° C.

Additionally, the reaction period is in the range of 5 to 48 hours, preferably 15 to 24 hours.

In the step of (8), Compound (q) is added with a basic solvent, for example, such as aqueous 0.2N sodium hydroxide, and stirred to give the lactone-ring opening compound (Compound (u)):

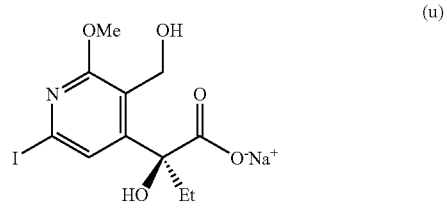

(u)

(wherein Me is a methyl group, and Et is an ethyl group.), which is soluble in the aqueous basic solution. When washing the solution with an organic solvent, a neutral-basic substance moves to an organic layer. The organic layer is separated, followed by acidification of the water layer with an acid and extraction with an organic solvent to recover Compound (q) in good purity.

The basic solvent is in the range of 0.01 to 5N, preferably 0.1 to 1N, more preferably 0.2 to 0.5N.

Illustrative of used bases are potassium hydroxide, calcium hydroxide, sodium hydroxide, potassium carbonate, sodium carbonate and the like, with sodium hydroxide being particularly preferable.

As an organic solvent any one can expediently be used if it is conventionally used. Illustrative of such solvent are dichloromethane, chloroform, ethyl acetate, toluene, diethyl ether, diisopropyl ether and the like, and in particular, with dichloromethane and chloroform being particularly preferable.

Illustrative of used acids are hydrochloric acid, sulfuric acid, nitric acid, acetic acid, phosphoric acid, trifluoroacetic acid and the like, with hydrochloric acid being particularly preferable.

In the step of (9), Compound (q) is dissolved in a high polarity solvent, and laminated with a low polarity solvent to precipitate crystals which are filtered. The filtrate is concentrated under reduced pressure to dryness. The obtained crystals are racemic, and a more optically purified Compound (q) is obtained as a residue.

As a high polarity solvent chloroform, dichloromethane, ethyl acetate, methanol, ethanol, propanol and the like can be used, and in particular, chloroform is preferable.

The used amount of a high polarity solvent, for example, in case of chloroform, is 1 to 10 ml, preferably 3 to 6 ml, against Compound (q) 1 g.

Illustrative of low polarity solvent are n-hexane, n-heptane, diethyl ether and the like, with n-hexane being particularly preferable.

The ratio of a high polarity solvent: a low polarity solvent is, for example, in case of chloroform:n-hexane, is in the range of 10:1 to 1:20, preferably 2:1 to 1:2.

The temperature in the crystallization procedure is not more than room temperature, preferably not more than 5° C.

In the step of (10), Compound (q) is dissolved in 1-propanol, added with a palladium catalyst and a base, and reacted under a carbon monoxide gas atmosphere to afford Compound (r).

As to a palladium catalyst, palladium acetate, tetrakis-(triphenylphosphine)palladium, dichlorobis-(triphenylphosphine)palladium, palladium chloride and the like can expediently be used, and palladium acetate is preferable particularly in view of the reactivity.

The used amount of a palladium catalyst is in 0.005 to 0.5 equivalent based on that of Compound (q), preferably 0.01 to 0.1 equivalent.

As a base any one can expediently be used if it is conventionally used. Illustrative of such bases are, for example, sodium carbonate, potassium carbonate, calcium carbonate, cesium carbonate, triethylamine (TEA), N,N-diisopropylethylamine (DIPEA), sodium hydroxide, potassium hydroxide and the like, with potassium carbonate being particularly preferable.

The used amount of a base, for example, in case of potassium carbonate, is in 1 to 20 equivalent based on that of Compound (q), preferably 4 to 10 equivalent.

The reaction temperature is in the range of 20° C. to a reflux temperature, preferably not more than 50° C. to a reflux temperature.

In the step of (11), Compound (r) is dissolved in solvent, added with a demethylation reagent, and reacted at room temperature to afford Compound (s).

As solvent acetonitrile, chloroform, dichloromethane, toluene and the like can be used, and in particular, acetonitrile is preferable.

Illustrative of demethylation reagents are chlorotrimethylsilane-sodium iodide, iodotrimethylsilane, hydriodic acid, hydrobromic acid and the like, with chlorotrimethylsilane-sodium iodide being particularly preferable.

The used amount of a demethylation reagent, for example, in case of chlorotrimethylsilane-sodium iodide, is in 1 to 10 equivalent based on that of Compound (r), preferably 2 to 5 equivalent.

In the step of (12), Compound (s) is dissolved in solvent, added with a base, and stirred under an inert gas atmosphere. The obtained mixture is dropped with t-butyl acrylate, and stirred under an inert gas atmosphere to afford Compound (t).

As to solvent, dimethyl sulfoxide (DMSO), N,N-dimethylformamide (DMF) and the like can expediently be used, and DMSO is preferable particularly in view of reactivity.

As a base potassium carbonate, sodium carbonate, sodium hydroxide, potassium hydroxide and the like can be used, and in particular, potassium carbonate is preferable.

The used amount of a base, for example, in case of potassium carbonate, is in 1 to 20 equivalent based on that of Compound (s), preferably 2 to 5 equivalent.

As an inert gas any one may be used in case it is a noble gas such as argon, helium, neon, krypton, xenon, radon or the like, or a gas of low receptivity such as nitrogen, and argon and nitrogen are preferable particularly in view of the cost.

The used amount of t-butyl acrylate is in 1 to 20 equivalent based on that of Compound (s), preferably 8 to 12 equivalent.

The reaction temperature is in the range of 20 to 80° C., preferably 40 to 60° C.

Further, the reaction period is in the range of 5 to 48 hours, and in particular, it is preferably not more than 24 hours in order to avoid particularly decomposition of Compound (t) produced.

In the step of (13), Compound (h) and Compound (e) are dissolved in solvent, added with an acid, and heated under an inert gas atmosphere and stirring to afford SN-38.

As solvent toluene, acetic acid and the like can expediently be used, and in particular, a toluene-acetic acid mix liquid is preferable.

As an inert gas any one may be used in case it is a noble gas such as argon, helium, neon, krypton, xenon, radon or the like, or a gas of low reactivity such as nitrogen, and argon and nitrogen are preferable particularly in view of the cost.

As an acid toluenesulfonic acid, methanesulfonic acid, trifluoroacetic acid and the like can be used, and toluenesulfonic acid is preferable particularly in view of reactivity.

The used amount of an acid, for example, in case of toluenesulfonic acid, is 1 to 100 mg based on that of Compound (h) 1 g, preferably 10 to 30 mg.

The used amount of Compound (e) is in 1 to 3 equivalent based on that of Compound (h), preferably 1 to 1.5 equivalent.

The reaction temperature is in the range of 50° C. to a reflux temperature, preferably 80° C. to a reflux temperature.

In the following, the invention will be illustrated in more detail by way of examples, but the invention is not limited to these.

EXAMPLE 1

Synthesis of Compound (b')

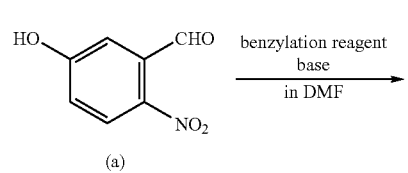
(a)

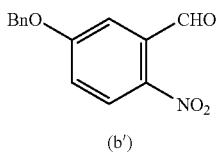

(b')

Wherein Bn is a benzyl group.

Compound (a) (38.5 g, 0.230 mol) was dissolved in 116 mL of DMF or acetone. Potassium carbonate (33.4 g, 0.242 mol, 2.1 eq.) and 27.8 mL (0.242 mol, 1.05 eq.) or 59.95 mL (0.461 mol, 2 eq.) of benzyl chloride were added to the stirred solution of Compound (a) at room temperature under argon atmosphere. After the addition, the mixture was heated at 60° C. and vigorously stirred for 20 hours with periodical checks the content of Compound (a). After Compound (a) was not detected anymore, the mixture was filtered by suction.

The solid material was washed with the same solvent used for the reaction. The filtrate and the washing were combined, and the solvent was evaporated under reduced pressure. And water (300 mL) was added to the residue. The mixture was stirred and the precipitates were filtered by suction and dried in air. After air-drying, the filtered material was dissolved in 170 mL of ethyl acetate. This solution was added to 1 L of hexane with stirring. The precipitated solid material was filtered by suction, washed with 300 mL of a mixture of ethyl acetate and hexane (1:10) and dried under reduced pressure.

Experiment (Exp.) 1 and 2, in which were discriminated by the amount of the benzyl chloride was varied and in Exp. 3, acetone was used as the reaction solvent.

TABLE 1

|        | Reaction solvent | Amount of benzyl chloride | Reaction time | Isolated yield |
|--------|------------------|---------------------------|---------------|----------------|
| Exp. 1 | DMF              | 1.05 eq.                  | 20 hours      | 94%            |
| Exp. 2 | DMF              | 2.00 eq.                  | 1 hour        | 94%            |
| Exp. 3 | acetone          | 2.00 eq.                  | 18 hours      | —              |

—: less than limit of detection

As shown in Table 1, 20 hours were required forth completion of the reaction with the yield of 94% when 1.05 eq. of benzyl chloride was used (Exp. 1). When 2.00 eq. of the benzyl chloride was used (Exp. 2), the reaction was finished in 1 hour and the yield was 94%. Three-fold amounts of DMF was minimal requirement for the reaction, otherwise the stirring was disturbed by precipitating the solid material during the reaction. When acetone was used as the reaction solvent, the reaction did not proceed even under reflux condition for 18 hours.

HPLC Operation Conditions

Column: Inertsil ODS-2, 5 μm, 4.6 mm ID×250 mm (GL science-made)

Temperature: constant temperature about 40° C.

Mobile phase: water:acetonitrile mixture (1:1)

Flow rate: 1 mL/min

Detect: 220 nm

EXAMPLE 2

Synthesis of Compound (c') (1)

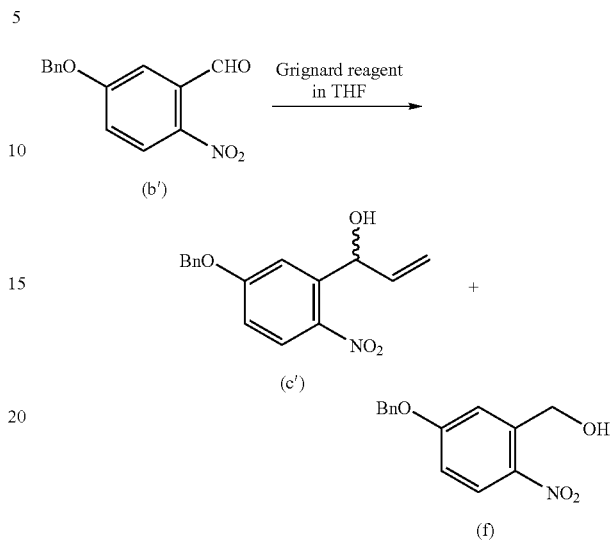

Wherein Bn is a benzyl group.

Compound (b') (1.0 g, 3.89 mmol) was dissolved in 20 mL of THF. Vinylmagnesium bromide (1.0 M THF solution, 5.84 mL, 5.84 mmol, 1.5 eq.) was added dropwise to the ice-cooled, stirred solution of Compound (b') under argon atmosphere over 15 minutes. During the addition, the internal temperature was kept within 3 to 10° C. After the stirring for 1 hour, the reaction solution was added to a saturated aqueous solution of ammonium chloride (20 mL) with stirring, and then to the solution 20 mL of ethyl acetate and 4 mL of hexane were added, and the obtained organic layer was washed with 20 mL of water and an aqueous saturated solution of sodium chloride successively, and dried over 3 g of sodium sulfate. The solvent was evaporated under reduced pressure to give Reaction product A.

A THF solution (20 mL) of Compound (b') prepared as mentioned above was added dropwise to an ice-cooled solution of vinylmagnesium bromide (1.0 M THF solution, 5.84 mL) under argon atmosphere over 15 minutes. During the addition, the internal temperature was kept within 3 to 10° C. After the stirring for 1 hour, the reaction solution was added to a saturated aqueous solution of ammonium chloride (20 mL) with stirring and then to the solution 20 mL of ethyl acetate and 4 mL of hexane were added, and the organic layer was separated and washed with 20 mL of water and a saturated aqueous solution of sodium chloride and dried over 3 g of sodium sulfate. The solvent was evaporated under reduced pressure to give Reaction product B.

Reaction product A and B were purified through silica gel column chromatography (ethyl acetate:hexane=1:20) to give Exp. 4 from Reaction product A and Exp. 5 from Reaction product B, respectively.

TABLE 2

|        | Yield of Compound (c') | Yield of Compound (f) (peak area %) |
|--------|------------------------|-------------------------------------|
| Exp. 4 | 84.0%                  | 3.5%                                |
| Exp. 5 | 26.8%                  | 11.3%                               |

As shown in Table 2, when the Grignard reagent was added to the solution of Compound (b'), the yield of the product increased by 57% and formation of Compound (f), a byproduct, was suppressed.

HPLC operation conditions; refer to the Example 1.

EXAMPLE 3

Synthesis of Compound (c') (2)

Compound (b') (1.0 g, 3.89 mmol) was dissolved in 10 to 100 mL of THF. Vinylmagnesium bromide (1.0 M in THF, 5.84 mL, 5.84 mmol, 1.5 eq.) was added dropwise to the stirred solution of Compound (b') under argon atmosphere over 15 minutes. After the stirring for 1 hour, the reaction solution was added to a saturated aqueous solution of ammonium chloride (20 mL) with stirring and then to the solution 20 mL of ethyl acetate and 4 mL of hexane were added, and the organic layer was separated and washed with 20 mL of water and a saturated aqueous solution of sodium chloride successively, and dried over 3 g of sodium sulfate. The solvent was evaporated under reduced pressure. The residue was purified by the same manner described in Example 2 (Exp. 4 and 5). Exp. 6 represents the results of the reaction at 20° C. using 20-fold amount of the solvent. Exp. 7 to 9 represent the results of the reaction at 3° C. using 10-fold, 40-fold, 100-fold amount of the solvent, respectively. The results of the reactions are summarized in Table 3.

TABLE 3

| | Reaction temperature | Amount of solvent | Yield of Compound (c') (peak area %) | Yield of Compound (f) (peak area %) |
|---|---|---|---|---|
| Exp. 4 | 3° C. | 20-fold | 84.0% | 3.5% |
| Exp. 6 | 20° C. | 20-fold | 68.7% | 4.8% |
| Exp. 7 | 3° C. | 10-fold | 81.1% | 5.7% |
| Exp. 8 | 3° C. | 40-fold | 88.6% | 3.5% |
| Exp. 9 | 3° C. | 100-fold | 90.2% | 2.8% |

As shown in Table 3, when the reaction was carried out at 10° C. or lower, more preferred 5° C. or lower, the formation of Compound (f) was suppressed and the yield of Compound (C') increased by 15% or more. When 100-fold amount of the solvent was used (Exp. 9), the formation of Compound (f) was suppressed and the yield of Compound (c') increased by 6%.

HPLC operation conditions; refer to Example 1.

EXAMPLE 4

Synthesis of Compound (d') (1)

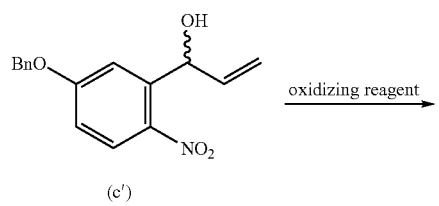

(c')

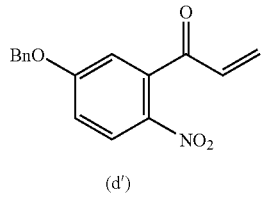

(d')

Wherein Bn is a benzyl group.

(1) Preparation of Manganese Dioxide:

An aqueous solution of manganese sulfate penta-hydrate (122 g/150 mL, 0.506 mol) and 117 mL of 40% sodium hydroxide were added to an aqueous solution of potassium permanganate (96.0 g/600 mL, 0.607 mol) at room temperature with stirring. After stirring for 18 hours, the solid material was filtered by suction and washed with water. The obtained solid material was dried in air to give 91.2 g of manganese dioxide.

(2) Synthesis of Compound (d')

Compound (c') (2.00 g, 7.02 mmol) was dissolved in 20 mL of chloroform, dichloromethane or ethyl acetate. Manganese dioxide 8.00 g (4-fold amount, 92.0 mmol, 13 eq.) prepared by the above mentioned method was added to the vigorous stirred solution of Compound (c') at 25° C. under argon atmosphere. The mixture was vigorously stirred for 15 hours. After the starting material was not detected anymore, the mixture was filtered by suction. The obtained solid material was washed with 20 mL of chloroform. The filtrate and the washing were combined, and the solvent was evaporated under reduced pressure. Exp. 10 to 12 were obtained.

TABLE 4

| | Reaction solvent | Reaction time | Remained starting material (peak area %) | Yield |
|---|---|---|---|---|
| Exp. 10 | chloroform | 15 hours | — | 91% |
| Exp. 11 | dichloromethane | 3 hours | — | 79% |
| Exp. 12 | ethyl acetate | 24 hours | 8% | — |

—: less than limit of detection

As shown in Table 4, when chloroform or dichloromethane was used as the reaction solvent, Compound (d') was synthesized in good yields. In particular, the reaction time was shortened to one third when dichloromethane was used as the reaction solvent. On the other hand, Compound (c') was remained even after 24 hours when ethyl acetate was used.

EXAMPLE 5

Synthesis of Compound (d') (2)

An aqueous solution of sodium hypochlorite (available chlorine min. 5.0%; 42 mL) and sodium hydrogen carbonate aqueous solution (7.1 g in 60 mL of water) were added to a vigorously stirred, ice-cooled mixture of 7.0 g (3.5 mmol) of Compound (c'), toluene (70 mL), ethyl acetate (70 mL), water (10 mL) and 38.3 mg (1 mol %) of TEMPO under ice cooling (at 2 to 6° C., 55 min). After 5 minutes, 0.4% (HPLC, peak area %) of the starting material was detected.

The mixture was placed still and the separated organic layer taken and was washed with a mixture of potassium iodide and potassium hydrogen sulfate (yellow→red-brown), a saturated aqueous solution of sodium thiosulfate and then water, successively. The solvent was evaporated under reduced pressure to give 6.4 g of Compound (d') (yield 91%, purity 92.6% by HPLC), which was purified by recrystallization from a mixture of methanol and water (25:1) to give 2.3 g of purified Compound (d') (starting from 3.0 g; purified Compound (d'), 2.3 g, recovery: 77%, purity: 95.2% by HPLC).

HPLC operation conditions; refer to Example 1.

EXAMPLE 6

Synthesis of Compound (e)

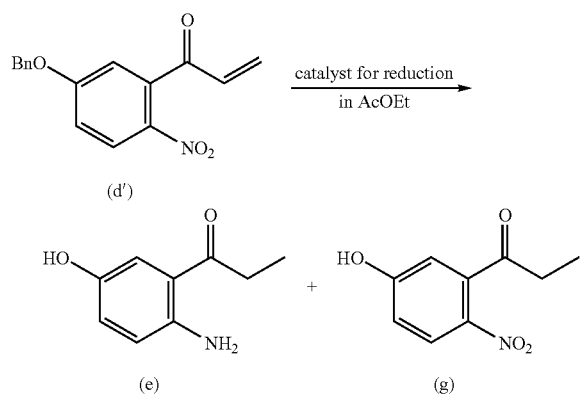

Wherein Bn is a benzyl group.

To an ice-cooled stirred solution of 1.84 g (6.50 mmol) of Compound (d') in 37 mL of ethyl acetate, 0.69 g (0.65 mmol, 10 mol %) of 10% palladium carbon was added under argon atmosphere. The mixture was vigorously stirred at 25° C. under hydrogen atmosphere and a part of the mixture was taken as a sample for HPLC, periodically. The reaction mixture was filtered and the filtrate was evaporated. Exp. 13 to 14 were obtained.

TABLE 5

| | Reaction time | Yield of Compound (e) | Yield of Compound (g) (peak area %) |
|---|---|---|---|
| Exp. 13 | 0.1 hour | 71% | 14% |
| Exp. 14 | 13 hours | 81% | 0% |

As shown in Table 5, the reaction was conducted for longer than 13 hours, the yield of Compound (e) increased by 10% and formation of the by-product, Compound (g), was suppressed.

HPLC Operation Conditions
Column: Inertsil ODS-2, 5 μm, 4.6 mm ID×250 mm (GL science-made)
Temperature: constant temperature about 40° C.
Mobile phase: water:acetonitrile mixture (1:1)
Flow rate: 1 mL/min
Detect: 254 nm

EXAMPLE 7

Whole Synthetic Process of 2'-amino-5'-hydroxypropiophenone

The whole synthetic process of 2'-amino-5'-hydroxypropiophenone is as follows.

(1) Synthesis of Compound (b')

Compound (a) (1.00 g, 5.98 mmol) was dissolved in 3 mL of DMF. Potassium carbonate (0.87 g, 6.28 mmol, 2.1 eq.) and 0.72 mL (6.28 mmol, 1.05 eq.) of benzyl chloride were added to the stirred solution of Compound (a) at room temperature under argon atmosphere. After the addition, the mixture was heated at 60° C. and vigorously stirred for 20 hours with periodical checks confirmation of the content of Compound (a) by HPLC. After Compound (a) was not detected anymore, the mixture was filtered by suction.

The solid material was washed with 3 mL of DMF. The filtrate and the washing were combined, and the solvent was evaporated under reduced pressure. After the evaporation, the residue was added to 100 mL of water. After the mixture was stirred for a while, the insoluble material was filtered by suction and dried in air. After the air-drying, the material was dried under reduced pressure (1 mmHg, at 20° C.) to give 1.45 g (yield 95%) of Compound (b') as pale yellow solid. The physical properties of Compound (b'), including NMR spectrum, are as follows.

Compound (b'); mp 71–73° C.
$^1$H-NMR (400 MHz, CDCl$_3$): δ 5.21 (2H, s, PhCH$_2$O), 7.21 (1H, dd, J=2.8, 9.3 Hz), 7.35–7.44 (6H, m), 8.16 (1H, d, J=9.3 Hz), 10.48 (1H, S, CHO).
IR (KBr): 1250, 1333, 1514, 1589, 1697 cm$^{-1}$.
EI-MS: m/z 257 (M$^+$).

(2) Synthesis of Compound (c')

Compound (b') (1.0 g, 3.89 mmol) was dissolved in 20 mL of THF. A solution of vinylmagnesium bromide (1.0 M in THF solution, 5.84 mL, 5.84 mmol, 1.5 eq.) was added dropwise over 15 minutes to the ice-cooled stirred solution of Compound (b') under argon atmosphere. During the addition, the internal temperature was kept within 3 to 10° C. After the stirring for 1 hour, the reaction solution was added to a stirred saturated aqueous solution ammonium chloride. Then 20 mL of ethyl acetate and 4 mL of hexane were added, and the organic layer was separated and washed with 20 mL of water and a saturated aqueous solution of sodium chloride and dried over 3 g of sodium sulfate. The solvent was evaporated under reduced pressure. The residue (1.19 g) was purified through silica gel column chromatography (ethyl acetate:hexane=1:20) to give 0.93 g of Compound (c') (yield 84%) as orange solid. The physical properties of Compound (c'), including NMR spectrum, are as follows.

Compound (c'); mp 60–63° C.
$^1$H-NMR (400 MHz, CDCl$_3$) δ: 5.15 (2H, s, PhCH$_2$O), 5.22–5.26 (1H, m), 5.39–5.44 (1H, m), 5.90 (1H, d, J=5.1 Hz), 6.06 (1H, ddd, J=5.1, 10.5, 15.6 Hz), 6.94 (1H, dd, J=2.9, 9.0 Hz), 7.34 (1H, d, J=2.9 Hz), 7.35–7.44 (5H, m), 8.04 (1H, d, J=9.0 Hz).
IR (KBr): 3298, 1614, 1582, 1506, 1292, 1229 cm$^{-1}$.
EI-MS: m/z 285 (M$^+$).

(3) Synthesis of Compound (d')

Compound (c') (2.00 g, 7.02 mmol) was dissolved in 20 mL of chloroform. Manganese dioxide (8.00 g, 4-fold amount, 92.0 mol, 13 eq.) was added to the vigorously stirred solution of Compound (c') at 25° C. under argon atmosphere. The mixture was vigorously stirred for 15 hours. After the starting material was not detected anymore, the mixture was filtered by suction. The obtained solid material was washed with 20 mL of chloroform. The filtrate and the washing were combined, and the solvent was evaporated under reduced pressure. The residue was purified through silica gel column chromatography (ethyl acetate:hexane=1:20) to give 1.88 g of Compound (d') (yield 95%) as white solid. The physical properties of Compound (d') including NMR spectrum are as follows.

Compound (d'); mp 84–85° C.
$^1$H-NMR (400 MHz, CDCl$_3$) δ: 5.17 (2H, s, PhCH$_2$O), 5.83 (1H, d, J=17.7 Hz), 6.01 (1H, d, J=10.6 Hz), 6.62 (1H, dd, J=10.6, 17.7 Hz), 6.91 (1H, d, J=2.7 Hz), 7.10 (1H, dd, J=2.7, 9.0 Hz), 7.37–7.43 (5H, m), 8.17 (1H, d, J=9.0 Hz).
IR (KBr): 1686, 1578, 1506, 1342, 1244 cm$^{-1}$.
EI-MS: m/z 283 (M$^+$).

(4) Synthesis of Compound (e)

To an ice-cooled stirred solution of 1.84 g (6.50 mmol) of Compound (d') in 37 mL of ethyl acetate, 0.69 g (0.65 mmol, 10 mol %) of 10% palladium carbon was added under argon atmosphere. The mixture was vigorously stirred at 25° C. under hydrogen atmosphere. After stirring for 13 hours, the catalyst was removed by filtration from reaction mixture. The filtrate was evaporated under reduced pressure to give 0.87 g (yield 81%, purity 91.14% by HPLC) of the crude product as orange solid. 500 mg of the obtained reaction product was purified through silica gel column chromatography (ethyl acetate:hexane=1:10→1:4) to give 421 mg of Compound (e) (yield 84%, purity 95.59% by HPLC) as yellow solid. The physical properties of Compound (e) including NMR spectrum are as follows.

Compound (e); mp 131–140° C.
$^1$H-NMR (400 MHz, CDCl$_3$) δ: 1.20 (3H, t, J=7.2 Hz), 2.93 (2H, q, J=7.2 Hz), 6.59 (1H, d, J=8.8 Hz), 6.88 (1H, dd, J=2.9, 8.8 Hz), 7.23 (1H, d, J=2.9 Hz).
IR (KBr): 3379, 3296, 1670, 1447, 1194 cm$^{-1}$.
EI-MS: m/z 165 (M$^+$).

EXAMPLE 8

Synthetic Method of Compound (e) without Protective Group R (1) Synthesis of Compound (c") from Compound (a)

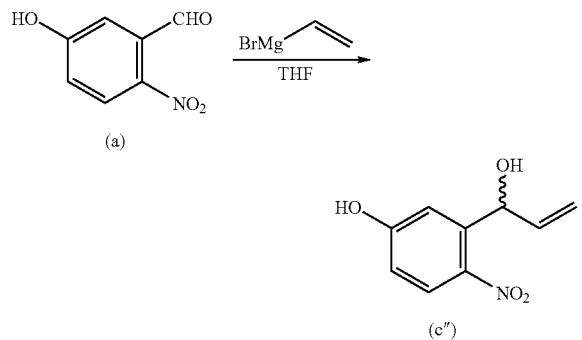

Compound (a) (500 mg, 2.99 mmol) was dissolved in 15 mL of THF. To the ice-cooled stirred solution of Compound (a), vinylmagnesium bromide (1.0 M in THF, 7.5 mL, 7.5 mmol, 2.5 eq.) was added dropwise over about 5 minutes under argon atmosphere. After the stirring for 1 hour, the reaction mixture was added to ice-cooled 1 mol/L hydrochloric acid (30 mL). Then 30 mL of ethyl acetate and 5 mL of hexane were added, and the organic layer was separated and washed with 50 mL of water and a saturated aqueous solution of sodium chloride and dried over 3 g of sodium sulfate. The solvent was evaporated under reduced pressure. The residue was purified through silica gel column chromatography (ethyl acetate:hexane=1:10→1:3) to give 541 mg of Compound (c") (yield 93%) as yellow-brown solid.

Compound (c");
$^1$H-NMR (400 MHz, CDCl$_3$) δ: 5.22–5.26 (1H, m), 5.35–5.40 (1H, m), 5.90–5.92 (1H, m), 6.06 (1H, ddd, J=5.2, 10.5, 15.6 Hz), 6.83 (1H, dd, J=2.7, 9.0 Hz), 7.19 (1H, d, J=2.7 Hz), 8.00 (1H, d, J=9.0 Hz).

(2) Synthesis of Compound (d") from Compound (c")

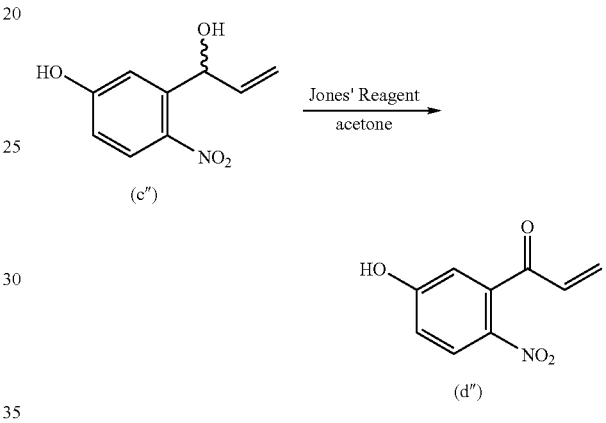

Compound (c") (1.00 g, 5.13 mmol) was dissolved in 8 mL of acetone. To the ice-cooled solution of Compound (c"), Jones reagent (3.0 mL, 5 mmol, 1.5 eq.) was added with stirring. After the stirring for 0.5 hours, three pieces of ice and a saturated aqueous solution of sodium hydrogen sulfate (5 mL) were added to the reaction mixture. Then 50 mL of ethyl acetate and 5 mL of hexane were added, and the layer was separately and washed with 50 mL of water and a saturated aqueous solution of sodium chloride successively and dried over 5 g of sodium sulfate. The solvent was evaporated under reduced pressure to give 0.82 g of Compound (d") (yield 83%).

Compound (d");
$^1$H-NMR (400 MHz, DMSO-d$_6$) δ: 5.84 (1H, d, J=17.6 Hz), 6.11 (1H, d, J=10.7 Hz), 6.60 (1H, dd, J=10.7, 17.7 Hz), 6.75 (1H, d, 2.7 Hz), 7.03 (1H, dd, 9.1 Hz), 8.13 (1H, d, J=9.1 Hz), 11.41(1H, s).

(3) Synthesis of Compound (e) from Compound (d")

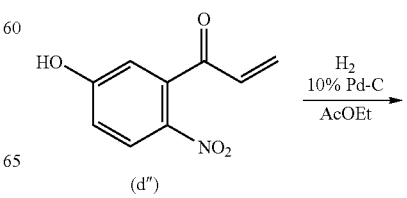

-continued

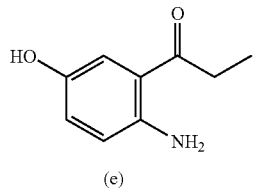

(e)

Compound (d″) (100 mg, 0.513 mmol) was dissolved in 1 mL of ethyl acetate. To the ice-cooled solution 55 mg (0.0513 mmol, 10 mol %) of 10% palladium carbon was added under argon atmosphere with stirring. The mixture was stirred at room temperature under hydrogen atmosphere for 18 hours. The catalyst was filtrated and the filtrate was evaporated under reduced pressure to give 64 mg of Compound (e) (yield 76%) as yellow solid.

EXAMPLE 9

Synthesis of 7-ethyl-10-hydroxycamptothecin (SN-38)

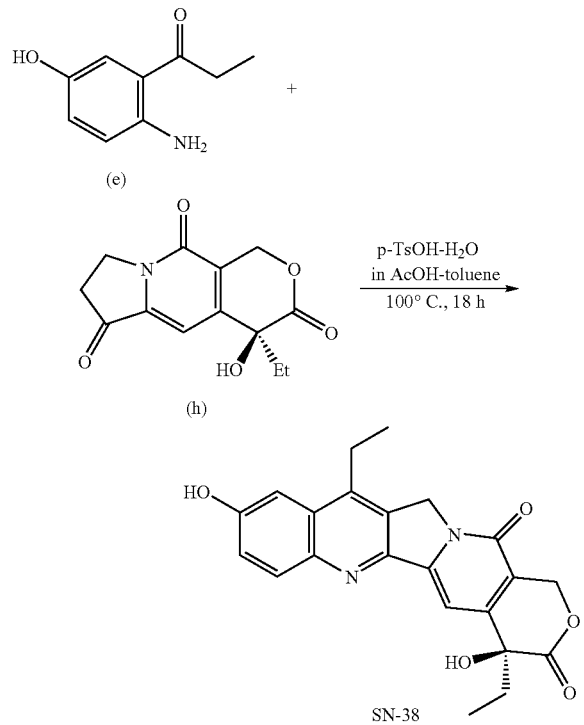

Compound (e) (0.36 g, 2.14 mmol) obtained in Example 7 and Compound (h) (0.50 g, 1.82 mmol) were suspended in a mixture of acetic acid and toluene (AcOH-toluene; 1:1, 10 mL). p-Toluenesulfonic acid monohydrate (p-TsOH.H₂O; 10 mg) was added to the suspension at room temperature, and the mixture was stirred at 100° C. for 18 hours. The reaction mixture was condensed under reduced pressure, toluene (10 mL) was added to the residue, and mixture was condensed under reduced pressure again. Acetone (9 mL) was added to the residue and the mixture was stirred at room temperature 2 hours, the insoluble material was filtered and washed with acetone (2 mL, twice). The filtered material was dried under reduced pressure to give SN-38 (0.63 g, purity 97.7% by HPLC, yield 89%) as black solid.

HPLC Operation Conditions

Column: Inertsil ODS-2, 5 μm, 4.6 mm ID×250 mm (GL science-made)

Temperature: constant temperature about 40° C.

Flow rate: 1 mL/min

Mobile phase: methanol-acetonitrile-10 mM potassium dihydrogenphosphate (1:1:3)

Detect: 254 nm

SN-38;

$^1$H-NMR (400 MHz, CDCl$_3$) δ: 0.98 (3H, t, J=7 Hz, CH$_3$), 1.38 (3H, t, J=7 Hz, CH$_3$), 1.90 (2H, q, J=7 Hz, CH$_2$), 3.08 (2H, q, J=7 Hz, CH$_2$), 5.17 (2H, s, CH$_2$O), 5.23 (1H, d, J=16 Hz), 5.54 (1H, d, J=16 Hz), 6.83 (1H, d, J=9 Hz), 7.34–7.39 (3H, m).

EXAMPLE 10

Synthesis of 7-ethyl-10-[4-(1-piperidino)-1-piperidino]carbonyloxycamptothecin (SN-38B-11)

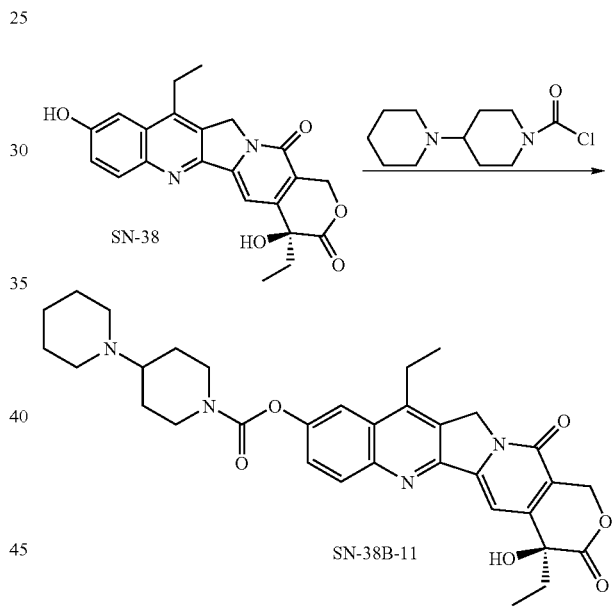

SN-38B-11 (1.22 g, 2.08 mmol, yield 89%, enantiopurity 99.8% ee) was obtained from SN-38 (0.91 g, 2.32 mmol) synthesized in Example 9 by the reported procedure (Sawada, S.; Okajima, S.; Aiyama, R.; Nokata, K.; Furuta, T.; Yokokura, T.; Sugino, E.; Yamaguchi, K.; Miyasaka, T. Chem. Pharm. Bull. 1991, 39, 1446.).

Chiral HPLC Operation Conditions

Column: DAICEL CHIRALCEL OD-H, 0.46 cmID×25 cm (#ODHOCE-AK031)

Guard cartridge: DAICEL CHIRALCEL OD-H, 0.4 cmID×1 cm

Injection amount: 10 μg/10 μL

Temperature: constant temperature about 40° C.

Flow rate: 1 mL/min

Mobile phase:dimethylamine:hexane:ethanol mixture (1:250:250)

Detect: 254 nm

EXAMPLE 11

Synthesis of 7-ethyl-10-[4-(1-piperidino)-1-piperidino]cabonyloxycamptothecin (CPT-11)

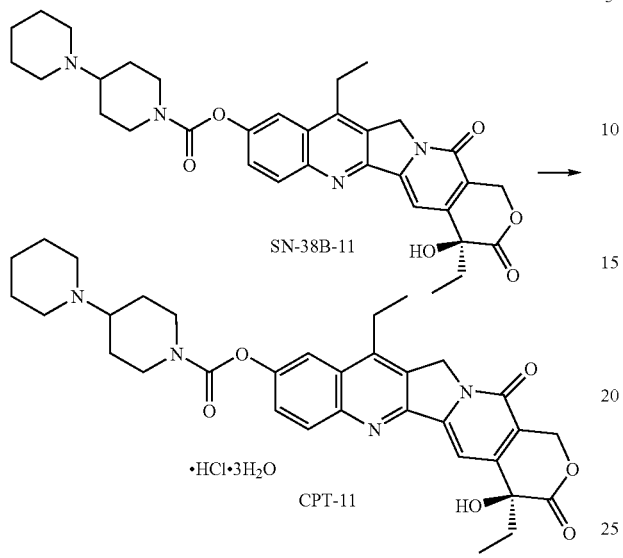

SN-38B-11 (1.00 g, 1.7 mmol) obtained in Example 10 was suspended in 1/10 N hydrochloric acid (20 mL, 2.0 mmol), and the suspension was heated at about 80° C. to dissolve in. Acetonitrile (100 mL) was added to the solution, and the mixture was stirred at room temperature for overnight. The precipitates were filtered, dried, and humidified under 75% RH afforded CPT-11 (0.95 mg, yield 89.8%) as pale yellow crystalline powder.

EXAMPLE 12

Synthesis of Compound (l) (1)

Compound (l) was obtained by formylation of Compound (k) at around −30° C. or −20° C. with n-butyl lithium and N-formyl-N,N',N'-trimethylethylenediamine following iodination at around −30° C. or −20° C. with n-butyl lithium and iodine.

Compound (k) (5.0 g; 0.028 mol) was dissolved in anhydrous THF (about 66 mL) under nitrogen gas atmosphere. The mixture was cooled at around −30° C. or −20° C. n-Butyllithium (1.6 mol/L in hexane; 21.2 mL, 0.034 mol, 1.2 eq.) was added dropwise to the solution and the mixture was stirred under cooling. Then N-formyl-N,N',N'-trimethylethylenediamine (4.4 g, 0.0034 mol, 1.2 eq.) was added to the reaction mixture as the formylation reagent and the mixture was at stirred under cooling.

n-Butyl lithium (1.6 mol/L in hexane; 35 mL, 0.05 mol, 1.2 eq.) was added dropwise to the mixture and stirred at the temperature shown in Table 6. Then iodine (18.4 g) in anhydrous THF (19 mL) was added dropwise to the stirred mixture.

An aqueous solution of sodium hydrogen sulfite (12 g in 200 mL) was added to the mixture. After stirring, the recovered organic layer (hexane) was analyzed by HPLC. The results were shown in Table 6.

HPLC Operation Conditions

Column: Capcell Pack ODS UG120, 4.6 mmID×150 mm

Mobile phase: 50 mM potassium dihydrogenphosphate: acetonitrile mixture (9:11)

Detect: 220 nm

Flow rate: about 1 mL/min

Temperature: room temperature

TABLE 6

| | Folmylation (° C.)[1] | Reaction time (hour) | Iodination (° C.)[1] | Reaction time (hour) | Compound (k)[3] | Compound (l)[3] | Yield (%)[4] |
|---|---|---|---|---|---|---|---|
| Exp. 15 | −48 to −30 <br> −32 to −29 | 3.0 | −70 to −65 <br> around −75 | 0.3 | NT[5] | 67.8 | 70.6 |
| Exp. 16 | −35 to −28 <br> around −35 | 1.0 | −30 to −20 <br> −35 to −25 | 0.5 | 5.9 | 67.8 | 71.9 |
| Exp. 17 | −20 to −15 <br> −20 to −15 | 2.0 | −10 to −5 <br> −10 to −5 | 0.5 | 6.2 | 70.5 | 66.7 |
| Exp. 18 | −10 to −5 <br> −10 to −5 | 3.0 | −10 to 0 <br> −10 to 0 | 0.5 | 3.4 | 77.6 | 63.7 |

[1] The upper lines show the actual internal temperature during the addition. The lower lines show the actual internal temperature range during the stirring.
[2] Exp. 15: the results of an experiment under the reported conditions
[3] Peak area %
[4] The yields were corrected by purity (HPLC; peak area %)
[5] NT: Not tested As shown in Table 6, Compound (l) was obtained in 60% yield or more when n-butyl lithium was used as the lithiation reagent.

As shown in Exp. 16, the reaction was proved to proceed at constant temperature at −40° C. to −30° C. in good yield (more than 70%).

EXAMPLE 13

Purification of Compound (l) (Washing with Diluted Hydrochloric Acid)

Compound (k) (5.0 g, 0.028 mol) was dissolved in anhydrous THF (about 66 mL). The reaction was carried out as described in Example 12 at constant temperature at around −35° C. Then-hexane layer obtained from the reaction mixture was washed with diluted hydrochloric acid (the same amount of the organic layer).

After the washing, the organic layer was dried over sodium sulfate, filtered and a part of the filtrate was analyzed by HPLC under the condition given in Example 12. The results were shown in Table 7.

TABLE 7

The analytical results of each the hexane layer after
washed with diluted hydrochloric acid

| hexane layer[1] (mL) | HCl (mol/L) | Residue (g) | Compound (k)[2] | MTPC[2,3] | Compound (l)[2] | Recovery (%) |
|---|---|---|---|---|---|---|
| 25 | —[4] | 1.5 | 6.0 | 11.8 | 54.7 | — |
| 50 | 0.1 | 2.9 | 6.6 | 12.4 | 58.7 | 100 |
| 50 | 1.0 | 2.6 | 1.8 | 13.0 | 61.2 | 100 |
| 50 | 2.5 | 2.6 | 0.4 | 12.6 | 62.4 | 100 |
| 50 | 3.5 | 2.6 | 0.2 | 12.7 | 64.2 | 100 |

[1] The hexane layer obtained from the reaction mixture was divided into 5 parts (25 mL for the intact mixture and 4 parts of 50 mL for washing). Each the 50 mL part was washed with diluted HCl listed in Table 7 and the recovered hexane layers were analyzed by HPLC.
[2] peak area %
[3] MTPC; 2-methoxy-6-trimethylsilylpyridine 3-carbaldehyde
[4] not washed As shown in Table 7, Compound (k) was almost removed by washing with the diluted hydrochloric acid. When 1.0 mol/mL and more concentrated hydrochloric acid was used for the washing, Compound (l) was obtained in good purity. 2-methoxy-6-trimethylsilylpyridine 3-carbaldehyde (MTPC), the formylated intermediate of Compound (k), was hardly removed by this method.

EXAMPLE 14

Purification of Compound (l) (Stepwise Washings with Diluted Hydrochloric Acid)

Compound (k) (5.0 g, 0.028 mol) was dissolved in anhydrous THF (about 66 mL). The reaction was carried out as described in Example 12 at constant temperature at around −35° C. The n-hexane layer obtained from the reaction mixture was washed in turn (top to bottom) with the diluted hydrochloric acid listed in Table 8 (the same amount of the organic layer).

After the washing, the aqueous acidic layer was separated, neutralized with sodium carbonate and then extracted with n-hexane. The organic layer was dried over magnesium sulfate, filtered and a part of the filtrate was analyzed by HPLC under the conditions given in Example 12. The results are summarized in Table 8.

TABLE 8

The analytical results on the hexane extracts from
the neutralized aqueous layer, which was obtained by washing
the original hexane layer with diluted hydrochloric acid in order
as follows (top to bottom).

| HCl (mol/L) | Residue (g)[1] | Compound (k)[2] | Compound (l)[2] | Recovery (%) |
|---|---|---|---|---|
| Washing with water | — | NT[3] | NT | — |
| 0.1 | 0.40 | 24.9 | 10.7 | — |
| 0.1 | 0.04 | NT | NT | — |
| 1.0 | 0.21 | 67.0 | 13.7 | — |
| 2.5 | 0.28 | 71.0 | 3.0 | — |
| 5.0 | 0.54 | 13.0 | 4.0 | — |
| Residue[4] | 7.27 | ND[5] | 77.9 | 98.3 |

[1] Each the diluted HCl washing was neutralized with sodium carbonate and the mixture was extracted with n-hexane. The organic layer was dried, filtered and the filtrate was evaporated under reduced pressure to dryness.
[2] HPLC (peak area %)
[3] Not tested
[4] The residue of the hexane layer after the stepwise washings.
[5] Not detected: less than limit of detection As shown in Table 8, the hexane layer was conveniently purified by multi step washings with hydrochloric acid of different concentrations to give Compound (l) with high purity.

EXAMPLE 15

Purification of Compound (l) (Purification by Distillation)

Compound (k) (5.0 g, 0.028 mol) was dissolved in anhydrous THF (about 66 mL). The reaction was carried out as described in Example 12 at constant temperature at around −35° C. The obtained reaction mixture (n-hexane layer) was recovered and distilled at 81 to 99° C. under reduced pressure (around 0.35 mmHg). After distillation, the residue in the distillation vessel was purified through silica gel column chromatography with n-hexane, and then a mixture of n-hexane and ethyl acetate (50:1) to give the purified product.

The residue and the purified material were analyzed by HPLC under the conditions below. The results are shown in the table 9.

HPLC Operation Conditions
Column: Capcell Pack ODS UG120, 4.6 mmID×150 mm
Mobile phase: 50 mM potassium dihydrogenphosphate: acetonitrile mixture (1:1)
Wave length: 220 nm
Flow rate: about 1 mL/min
Temperature: room temperature

TABLE 9

The analytical results on the fractions of the residue of the hexane layer by distillation

|  | (g) | Compound (k)[1] | MTPC[1] | Compound (l)[1] | Recovery (%) |
|---|---|---|---|---|---|
| Intact mixture | — | 3.6 | 13.5 | 71.5 | — |
| Fraction-1 | 0.19 | 47.3 | 36.1 | 8.7 | — |
| Fraction-2 | 1.16 | 8.9 | 53.7 | 28.8 | — |
| Trap | 1.17 | 70.3 | ND[2] | ND | — |
| Residue | 5.13 | 0.3 | 3.1 | 89.9 | 75.9 |
| Purified product[3] | — | — | 3.9 | 95 | |

[1] peak area %
[2] Not detected: less than detection limit
[3] The final residue was purified through silica gel column chromatography As shown in Table 9, MTPC was almost removed by distillation. Further purification by silica gel column chromatography afforded Compound (l) with excellent purity. It is not preferred that the distillation at higher temperature than that in Table 9 because the coloration and decomposition of Compound (l) were observed.

EXAMPLE 16

Purification of Compound (l) (Recovery as Hydrochloric Acid Salt)

Compound (k) (5.0 g, 0.028 mol) was dissolved in anhydrous THF (about 66 mL). The reaction was carried out as described in Example 12 at constant temperature around −35° C. The reaction mixture (10 g) was dissolved in 10 N hydrochloric acid (10 mL) and stirred at room temperature. The yellow precipitates were filtered and washed with a small amount of 10 N hydrochloric acid and the material was dissolved in water (about 10 mL). The pH of the aqueous solution was adjusted to about 8 by adding sodium hydrogen carbonate, and the mixture was extracted with hexane and the organic layer was evaporated under reduced pressure to dryness.

The residue was analyzed by HPLC under the conditions given in Example 15. The results are shown in Table 10.

TABLE 10

The analytical results on the extracts by neutralizing the hydrochloric acid salt obtained in 10 mol/L hydrochloric acid.

|  | (g)[1] | MTP[2] | MTPC[2] | Compound (l)[2] | Recovery (%) |
|---|---|---|---|---|---|
| Pre-purified | 10 | —[3] | 16.9 | 61.8 | — |
| Post-purified | 6 | — | 3.3 | 90.0 | 87.4 |

[1] the weight of the residue
[2] peak area %
[3] Not tested

As shown in Table 10, the crude reaction product was collected as the hydrochloric acid salt and the salt was recovered as Compound (l) by neutralization, MTPC was almost removed by this method.

Compound (l): yellow oil.
$^1$H-NMR (499 MHz, CDCl$^3$) δ: 0.30 (9H, s) 4.05 (3H,s), 7.67 (1H, s), 10.19(1H, s),
EI: MS:m/z 335 (M$^+$).

EXAMPLE 17

Synthesis of Compound (m)

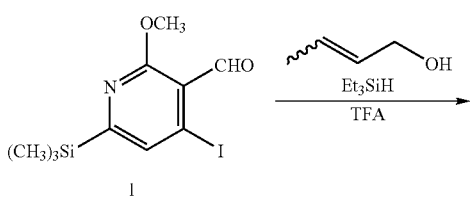

l

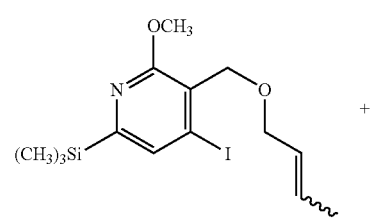

m

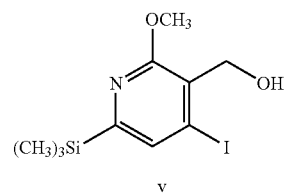

v

To a mixture of Compound (l) (20.0 g, 56.0 mmol, content: 93.9% by HPLC), triethylsilane, (17.9 mL, 112.0 mmol, 2 eq.) and crotyl alcohol (15.7 mL, 184.8 mmol, 3.3 eq.), trifluoroacetic acid (28.5 mL, 375.3 mmol, 6.7 eq.) was added dropwise at 0 to 5° C. under nitrogen gas atmosphere with stirring. After stirring at the temperature for 30 min, the mixture was stirred at ambient temperature for 20 hrs. An aqueous solution of sodium carbonate (20.8 g in 277 mL of water) and n-hexane (56 mL) were added to the mixture and the organic layer was separated and the aqueous layer was extracted with n-hexane (56 mL). The combined organic layers were evaporated under reduced pressure to dryness. The residue was purified through silica gel column chromatography; silica gel (80 g, Fuji Silysia PSQ100B) with a mixture of n-hexane-ethyl acetate (73:3) as the eluent.

The results of this Example is summarized Table 11 (Exp. 20). Exp. 19 in the table shows the results of a trace experiment under the reported conditions; Josein, H.; Ko, S. B.; Bom, D.; Curran, D. P., Chem. Eur. J. 1998, 4, 67–83. Curran, D. P.; Ko, S. B.; Josein, H., Angew. Chem. Int. Ed. Engl. 1995, 34, 2683–2684. Under the reported conditions, dichloromethane was used as the reaction solvent. The equal level of the product (m) was obtained in the quality and yield without dichloromethane.

TABLE 11

| | Solvent | Time (h) | HPLC (% peak area) | | | |
| --- | --- | --- | --- | --- | --- | --- |
| | | | (l) | (m) | (v) | others |
| Exp. 19 | CH$_2$Cl$_2$ | 17 | 1.19 | 68.08 | 16.94 | 13.79 |
| Exp. 20 | neat | 20 | 0.40 | 64.38 | 24.40 | 10.82 |

HPLC Operating Conditions
Column: GL Science Inertsil ODS-2, 0.46 cm ID × 25 cm
Temperature: Constant temperature at around 40° C.
Flow rate: 1 mL/min
Mobile phase: acetonitrile - 10 mM potassium dihydrogenphosphate (5:1)
Detect: 254 nm

EXAMPLE 18

Synthesis of Compound (l) (2)

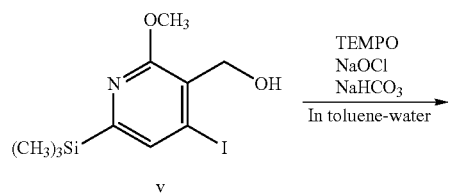

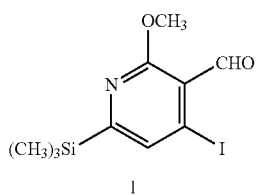

To a mixture of Compound (v) (1.00 g, content; 98.43%, 2.9 mmol), TEMPO (2.3 mg, 0.015 mmol, 0.005 eq.) and 7% (w/v) sodium hydrogen carbonate (7.0 mL) in toluene (8.7 mL), an aqueous solution of sodium hypochlorite (available chlorine; minimal 5%, 4.5 g, 3.0 mmol, 1.05 eq.) was added at 0 to 5° C. and then the mixture was stirred at 0 to 5° C. for 2 hrs. 10% sodium sulfite (3.7 mL, 2.9 mmol) was added to the mixture and the resulting mixture was stirred at 0 to 5° C. for 30 min. The insoluble material in the mixture was removed by filtration and the material on the filter paper was washed with toluene (1 mL×3). The organic layer of the filtrate was separated and washed with water (10 mL), dried over sodium sulfate (2 g), filtered and the desiccant was washed with toluene. The filtrate and the washing were combined and then evaporated under reduced pressure to dryness. Compound (l): yellow oil, 0.93 g (87% yield), content: 90.60% by HPLC (see Example 17).

EXAMPLE 19

Synthesis of Compound (n) (1)

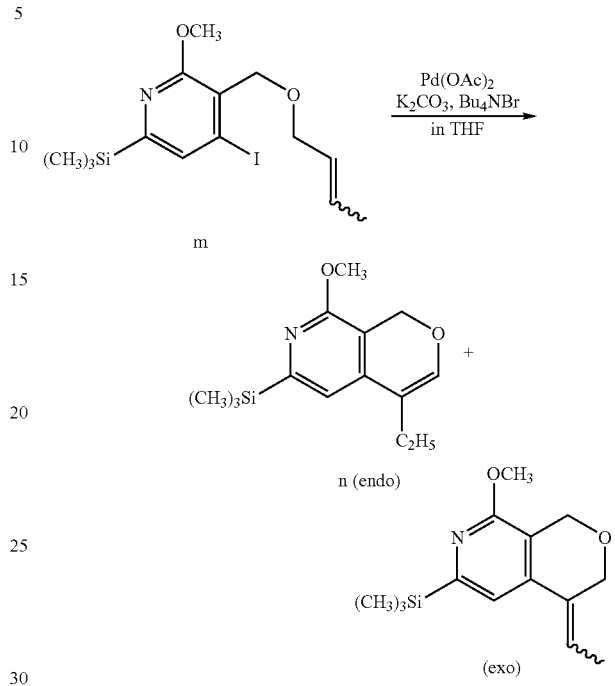

Compound (m) (1.60 g) was dissolved in the solvents listed in Table 12, tetrabutylammonium bromide (0.83 g), potassium carbonate (0.71 g) and palladium acatate (57 mg) were added to the solution. Each the reaction was conducted under the conditions directed in Table 12.

The reaction mixture was poured into ice-cooled n-hexane (18 mL) with stirring. The insoluble material was filtered by suction and the material was washed with n-hexane (6 mL×3). The filtrate and the washing were combined and washed with water (9 mL×2), dried over anhydrous sodium sulfate and then evaporated under reduced pressure to dryness. The residue was purified through silica gel column chromatography with n-hexane-ethyl acetate (95:5) as the eluent.

Exp. 21 in Table 12 was the results of an experiment conducted under the reported conditions; Josien, H.; Ko, S. B.; Bom, D.; Curran, D. P., Chem. Eur. J. 1998, 4, 67–83. Curran, D. P.; Ko, S. B.; Josien, H., Angew. Chem. Int. Ed. Engl. 1995, 34, 2683–2684.

The ratio of the endo and exo forms of each the purified product was measured by HPLC. As shown in Table 12, satisfactory selectivity (endo-exo ratio) and isolated yield were obtained when THF was used as the reaction solvent under refluxed conditions (Exp. 25–27). The isolated yields of (Exp. 25–27) were higher than that of the reported conditions (Exp. 21) by 10% or more.

TABLE 12

| | Solvent | Temperature | Time (h) | Ratio | Yield (%) |
| --- | --- | --- | --- | --- | --- |
| Exp. 21 | DMF | 85° C. | 1.5 | 2.3 | 69 |
| Exp. 22 | CHCl$_3$ | Reflux | 5.0 | 3.1 | — |
| Exp. 23 | Tol | 85° C. | 96.0 | 3.7 | — |
| Exp. 24 | MeCN | 85° C. | 2.0 | 4.3 | — |
| Exp. 25 | THF | Reflux | 4.0 | 6.6 | 79 |

TABLE 12-continued

| | Solvent | Temperature | Time (h) | Ratio | Yield (%) |
|---|---|---|---|---|---|
| Exp. 26 | THF | Reflux | 5.0 | 7.0 | 84 |
| Exp. 27 | THF | Reflux | 4.0 | 7.1 | 82 |

DMF: N,N-dimethylformamide,
Tol: toluene,
MeCN: acetonitrile,
THF: tetrahydrofuran,
Ratio: peak area of endo form/peak area of exo form (HPLC),
Yield: isolated yield,
—: not determined,
HPLC operating conditions; see Example 17.

EXAMPLE 20

Synthesis of Compound (n) (2)

To a solution of Compound (m) (1.27 g, 2.6 mmol, content; 78.7%) in a mixture of diisopropyl ether-acetonitrile-water (4:3:1, 20 mL), tetrabutylammonium bromide (0.82 g, 2.6 mmol), N,N-diisopropylethylamine (3.48 mL, 20.8 mmol, 8 eq.) and palladium acetate (57 mg, 0.26 mmol) were added and the resulting mixture was heated under reflux for 30 min. After cooling the inner temperature to 20° C. or below, the insoluble material in the mixture was filtered by suction and the filtered material was washed with n-hexane (2.6 mL×3). To the combined filtrate and the washing, n-hexane (10 mL) and 10% sodium sulfite (16 mL, 13.0 mmol, 5 eq.) were added. The organic layer was separated and washed with 1 N hydrochloric acid (16.4 mL) and then water (10 mL×2), continuously. The organic solution was evaporated under reduced pressure to dryness. Compound (n); tanned oil, 0.83 g (91% yield), content: 73.3% by HPLC (see Example 17), endo-exo ratio: 10.6.

Thus, the selectivity was markedly improved as compared with that of Exp. 21 in Table 12. The isolated yield was also improved by 20% of that of Exp. 21 in Table 12.

EXAMPLE 21

Synthesis of Compound (o)

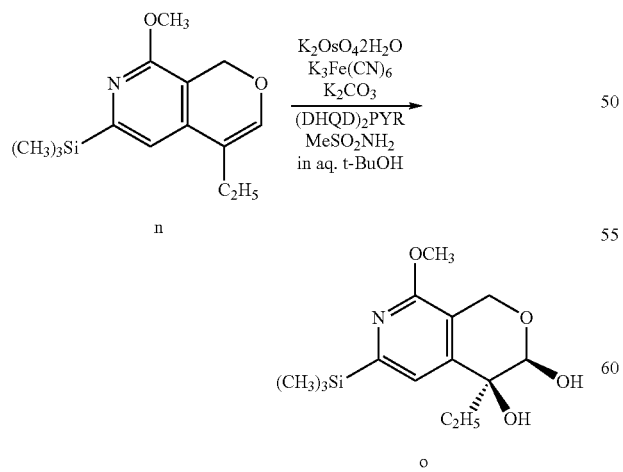

To a solution of potassium fericyanide (195.7 g, 0.59 mol), potassium carbonate, (82.1 g, 0.59 mol) and methanesulfonamide (37.7 g, 0.40 mol) in water (990 mL), (DHQD)$_2$PYR (4.36 g, 4.95 mmol) and potassium osmate (VI) dihydrate (1.0 mmol) were added and the mixture was stirred at aroud 5° C. for 1 hr. To the stirred mixture, Compound (n) (77.8 g, 0.18 mol, content: 61.5%) was added and the resulting mixture was stirred at the temperature for additional 20 hrs. Powdered sodium sulfite (74.9 g) was added to the mixture and the stirring was continued at the temperature for 30 min. The insoluble material in the mixture was filtered on a Celite pad and the material on the pad was washed with ethyl acetate (4 times, total 770 mL). The organic layer of the filtrate was separated and the aqueous layer was further extracted with ethyl acetate (770 mL). The combined organic layers were dried over anhydrous sodium sulfate, filtered, and evaporated under reduced pressure to dryness. The residue was purified through silica gel column chromatography with a mixture of dichloromethane-ethyl acetate (4:1) as the eluent; silica gel (280 g, Fuji Silysia PSQ100B). Compound (o); umber solid.

As shown in Table 13, using potassium osmate as the oxidant effected the equal level of the isolated yield and enantio excess in place of highly volatile osmium (VIII) oxide.

TABLE 13

| | Oxidant | Yield (%) | % ee |
|---|---|---|---|
| Exp. 28 | OsO$_4$ | 82 to 95 | 95.6 to 96.2 |
| Exp. 29 | K$_2$OsO$_4$.2H$_2$O | 94 | 95.9 |

Exp. 28: conducted under the reported conditions; Josein, H.; Ko, S. B.; Bom, D.; Curran, D. P., Chem. Eur. J. 1998, 4, 67–83. Curran, D. P.; Ko, S. B.; Josein, H., Angew. Chem. Int. Ed. Engl. 1995, 34, 2683–2684.

% ee: Compound (o) obtained here was converted into Compound (p) by the method described in Example 22 and its enantioexcess was measured by chiral HPLC method (see; Example 22)

EXAMPLE 22

Synthesis of Compound (p)

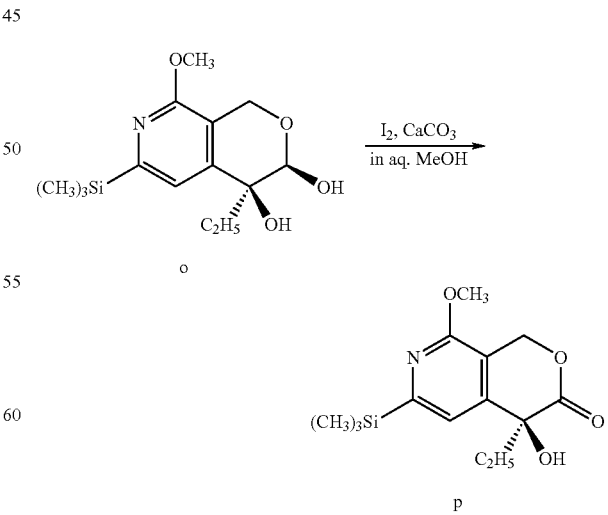

To a solution of Compound (o) (70 g) in a mixture of methanol and water (10:1, 1.0 L), iodine (the amount is given in Table 14) and powdered calcium carbonate (47.1 g) were added at ambient temperature with stirring. The reaction mixture was stirred at given temperature and period in Table 14.

One litter of 10% sodium sulfite and chloroform (1.0 L) were added to the mixture and the resulting mixture was stirred at ambient temperature for 30 min. The insoluble material was removed by filtration and the organic layer of the filtrate was separated. The aqueous layer was extracted with chloroform (500 mL×2). The extracts were combined, dried over anhydrous sodium sulfate, filtered and then evaporated under reduced pressure to dryness.

Using 4 equivalent of iodine under reflux conditions, this reaction was completed in 5 hrs, about one tenth of that of the reported conditions with comparable yields.

TABLE 14

|  | Iodine (eq.) | Temperature | Time (hr) | Yield (%) |
|---|---|---|---|---|
| Exp. 30 | 9 | Ambient | 48 | 86 |
| Exp. 31 | 4 | Ambient | 72 | 86 |
| Exp. 32 | 4 | 40° C. | 48 | 88 |
| Exp. 33 | 4 | 60° C. | 20 | 88 |
| Exp. 34 | 4 | Reflux | 5 | 84 |

Exp. 30: conducted under the reported conditions;
Josien, H.; Ko, S. B.; Bom, D.; Curran, D. P., Chem. Eur. J. 1998, 4, 67–83.
Curran, D. P.; Ko, S. B.; Josien, H., Angew. Chem. Int. Ed. Engl., 1995, 34, 2683–2684.
Yield (%): isolated yields Yield (%): isolated yields HPLC Operation Conditions Column: GL Science Inertsil ODS-2, 0.46 cm ID×25 cm Temperature: constant temperature at around 40° C.

Flow rate: 1 mL/min

Mobile phase: 10 mM potassium dihydrogenphosphate-acetonitorile (4:3)

Detect: 254 nm

Chiral HPLC Operating Conditions

Column: DAICEL CHIRALCEL OD-H, #ODH0CE-AK031, 0.46 cm ID×25 cm

Guard cartridge: DAICEL CHIRALCEL OD-H, 0.4 cm ID×1 cm

Temperature: constant temperature at around 25° C.

Flow rate: 0.5 mL/min

Mobile phase: a mixture of n-hexane-ethanol (200:1)

Detect: 254 nm

EXAMPLE 23

Synthesis of Compound (q)

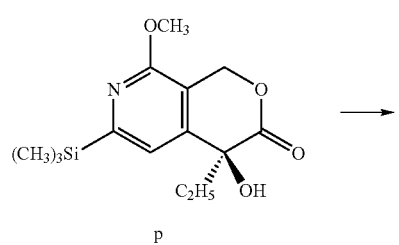

p

-continued

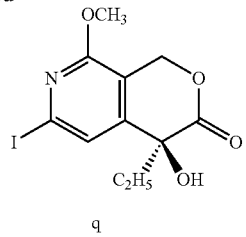

q

To a solution of Compound (p) (50.2 g) in the solvent (about 400 mL; given in Table 15), the reagents in the table were added and the resulting mixture was stirred at the given temperature for the hours. To the reaction mixture 20% sodium carbonate (1.7 L), 10% sodium sulfite (1.0 L) and chloroform (550 mL) were added with stirring. The organic layer was separated and the aqueous layer was extracted with chloroform (550 mL×2). The extracts were combined, dried over anhydrous sodium sulfate, filtered and then evaporated under reduced pressure to dryness. The content of Compound (q) in the residue was quantified by HPLC. The results are summarized in Table 15.

This conversion was satisfactorily performed by using NCS—NaI at 65° C. in acetic acid (Exp. 39). The period required for the completion was apparently shortened and the yields of Compound (q) under the conditions were higher than that of the report [Comparative Experiment 1 (Com. 1)] by 50% or more.

TABLE 15

|  | Solvent | Reagent | Eq. | Temperature | Time (hr) | Yield (%) |
|---|---|---|---|---|---|---|
| Com. 1 | *) | ICl | 4 | RT to 40° C. | 48 | 45 |
| Exp. 35 | AcOH | NIS | 12 | 65° C. | 45 | 63 |
| Exp. 36 | CH$_2$Cl$_2$ | I$_2$-CF$_3$CO$_2$Ag | 2 | Ambient | 17 | 97 |
| Exp. 37 | AcOH | NCS-NaI | 6 | 65° C. | 16 | 95 |
| Exp. 38 | AcOH | NCS-NaI | 6 | 65° C. | 16 | 93 |
| Exp. 39 | AcOH | NCS-NaI | 6 | 65° C. | 15 | 94 |

*) a mixture of dichloromethane and chloroform (3:2),
AcOH: acetic acid,
ICl: iodine monochloride,
NIS: N-iodosuccinimide,
NCS: N-chlorosuccinimide,
Eq.: molar ratio of the reagent(s) employed,
Yield: isolated yields.

EXAMPLE 24

Purification of Compound (q) (1)

Compound (q) (63 g, Purity 89.2% by HPLC) obtained in Example 23 was suspended in methanol (150 mL), to the suspension was added dropwise 0.2 N sodium hydroxide with vigorous stirring and the stirring was continued for 2 hrs. The alkaline solution was washed with chloroform (400 mL×3) and the pH of the aqueous layer was adjusted with 6 N hydrochloric acid to 1–2 and the acidified solution was extracted with chloroform (400 mL×3). The chloroform layer was dried over anhydrous sodium sulfate, filtered and then evaporated under reduced pressure to dryness. Compound (q) (Exp. 40); purity 97.7% (% peak area; HPLC operating conditions: see Example 25)

EXAMPLE 25

Purification of Compound (q) (2)

Compound (q) (50 g) purified by the method described in Example 24 was dissolved in chloroform (240 mL) and n-hexane (400 mL) was softly added on the surface of the solution. The mixture was left to stand at ambient temperature for 15 hrs. The precipitates of the mixture were removed by filtration and the filtrate was evaporated under reduced pressure to dryness (Exp. 41).

Compound (q) (Exp. 40) obtained in Example 24 (93–96% enantioexcess) was optically purified by this method. Compound (q) (Exp. 41) obtained here exhibited 99.7–99.9% enantioexcess by the chiral HPLC given below.

HPLC Operating Conditions
Column: GL Science Inertsil ODS-2, 0.46 cm ID×25 cm
Temperature: constant temperature at around 40° C.
Flow rate: 1 mL/min
Mobile phase: a mixture of acetonitrile-10 mM potassium dihydrogenphophate (5:3)
Detect: 254 nm
Chiral HPLC Operating Conditions
Column: DAICEL CHIRALPAK AD-H, # ADH0CE-BC037, 0.46 cm ID×25 cm
Guard cartridge: DAICEL CHIRALPAK AD-H, 0.4 cm ID×1 cm
Temperature: constant temperature at around 25° C.
Flow rate: 1 mL/min
Mobile phase: a mixture of n-hexane-2-propanol (25:1)
Detect: 254 nm

EXAMPLE 26

Synthesis of Compound (r)

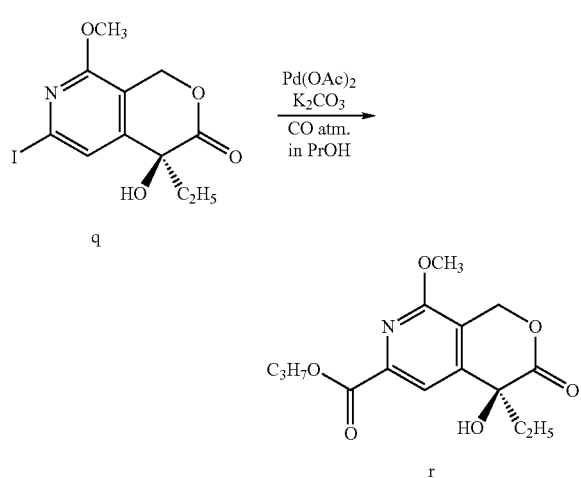

A solution of Compound (q) (42.8 g, 0.10 mol, content: 84.5%), palladium acetate (1.34 g, 6.0 mmol) and potassium carbonate (24.7 g, 0.18 mol) in propanol (490 mL) was charged in a reaction vessel. The vessel was degassed by suction and released with nitrogen gas, and degassed again by suction and then replaced with carbon monoxide. The mixture was stirred at 60° C. under carbon monoxide atmosphere for 18 hrs. The insoluble material was filtered on a Celite pad and the material was washed with ethyl acetate (300 mL). To the filtrate, 1 N hydrochloric acid (150 mL) and brine (300 mL) were added and the mixture was shaken vigorously. The organic layer was separated and the aqueous layer was extracted with ethyl acetate (300 mL). The combined organic layers were dried over anhydrous sodium sulfate, filtered and then evaporated under reduced pressure to dryness. The residue was purified through silica gel column chromatography; silica gel (100 g, Fuji Silysia PSQ100B) with a mixture of chloroform and methanol (99:1) as the eluent. Compound (r): umber oil, 30.3 g (70% yield), content: 73.4% quantified by HPLC.

HPLC Operating Conditions
Column: GL Science Inertsil ODS-2, 0.46 cm ID×25 cm
Temperature: constant temperature at around 40° C.
Flow rate: 1 mL/min
Mobile phase: 10 mM potassium dihydrogenphosphate-acetonitrile (4:3)
Detect: 254 nm

EXAMPLE 27

Synthesis of Compound (s)

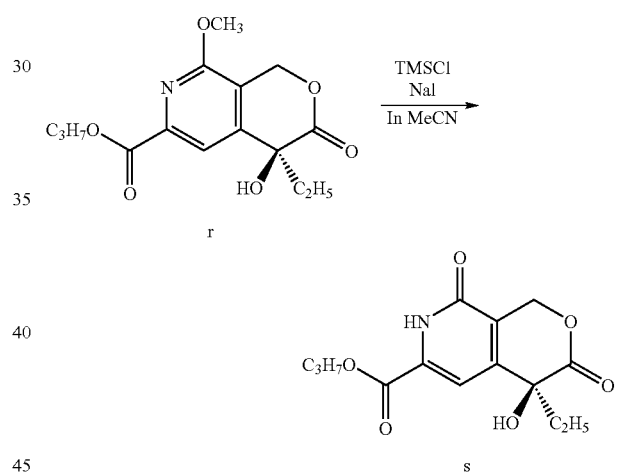

To a stirred solution of Compound (r) (28.7 g, 68.2 mmol, content: 73.4%) and sodium iodide (27.6 g, 0.18 mol) in absolute acetonitrile (141 mL), chlorotrimethylsilane (23.3 mL, 0.18 mmol) was added dropwise at ambient temperature under nitrogen gas atmosphere. The mixture was stirred at ambient temperature for 3 hrs. To the mixture, 1 N hydrochloric acid (8 mL) and 10% sodium sulfite (232 mL) were added and the resulting mixture was stirred for 30 min. The mixture was extracted with ethyl acetate and the organic layer was separated and evaporated under reduced pressure to dryness. Compound (s): 22.3 g (95% yield), content: 85.6% quantified by HPLC (as follows).

HPLC Operating Conditions
Column: GL Science Inertsil ODS-2, 0.46 cm ID×25 cm
Temperature: constant temperature at around 40° C.
Flow rate: 1 mL/min
Mobile phase: 10 mM potassium dihydrogen phosphate-acetonitrile (5:2).
Detect: 254 nm

EXAMPLE 28

Synthesis of Compound (t)

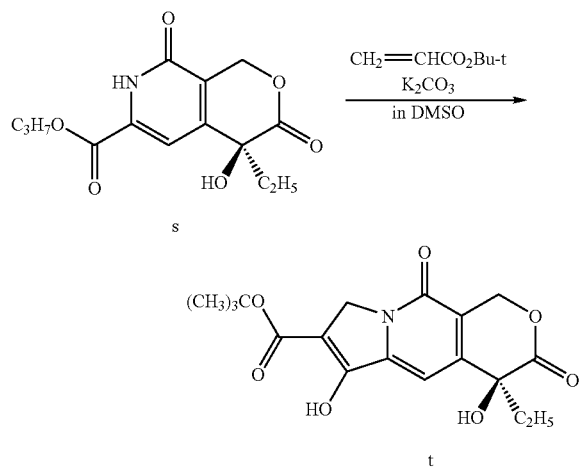

A solution of Compound (s) (0.50 g) in dimethylsulfoxide (DMSO, 7 mL) in the presence of an inorganic base (potassium or cesium carbonate, 0.4 g) was stirred at 50° C. under argon atmosphere for 20 min. To the stirred mixture tert-butyl acrylate (1.8 g) was added dropwise and the resulting mixture was stirred at 50° C. under argon atmosphere for 24 hrs. Water (10 mL) and concentrated hydrochloric acid (1 mL) were added to the ice-cooled mixture and the mixture was extracted with a mixture of toluene and ethyl acetate (4:1, 7 mL×4). The combined extracts were dried over anhydrous sodium sulfate, filtered and evaporated under reduced pressure to dryness (Exp. 42–43). The residue was assayed by HPLC (as follows).

As shown in Table 16, Compound (t) was obtained in 72% yield using cesium carbonate as the base (Exp. 42), on the other hand, inexpensive potassium carbonate was used as the base, the yield was equal level with the Exp. 42.

TABLE 16

| | Base | Yield (%) |
|---|---|---|
| Exp. 42 | $Cs_2CO_3$ | 72 |
| Exp. 43 | $K_2CO_3$ | 77 |

HPLC Operating Conditions
Column: GL Science Inertsil ODS-2, 0.46 cm ID×25 cm
Temperature: constant temperature at around 40° C.
Flow rate: 1 mL/min
Mobile phase: 10 mM potassium dihydrogenphosphate-acetonitrile (5:2)
Detect: 254 nm

EXAMPLE 29

Synthesis of SN-38

A mixture of Compound (h) (0.50 g, 1.82 mmol, content: 96.6%) and Compound (e) (0.36 g, 2.18 mmol) in a mixture of toluene-acetic acid (1:1, 10 mL) in the presence of p-TsOH.H₂O (10 mg) was heated at 90° C. with stirring under nitrogen gas atmosphere for 7 hrs. After cooling, the mixture was evaporated under reduced pressure to dryness. After 2 times of azeotoropic removal of acetic acid with toluene (10 mL), acetone (9 mL) was added to the residue and the suspension was stirred under nitrogen atmosphere for 30 min. The solid was collected by filtration, washed with acetone (2 mL×2) and then dried under reduced pressure. SN-38 (Exp. 45): ocherous solid, 0.63 g (89.1% yield), purity; 99.6% by HPLC (see Example 9).

Exp. 44 in Table 17 shows the results of an experiment under the reported conditions; Henegar, K. E.; Ashford, S. W.; Baughman, T. A.; Sih, J. C.; Gu, R. L., J. Org. Chem. 1997, 62, 6588–6597.

Under nitrogen gas atmosphere, the purity and yield of SN-38 are improved as shown in Table 17.

TABLE 17

| | | Purity (%) | Yield (%) |
|---|---|---|---|
| Exp. 44 | Open vessel | 97.6 | 75 |
| Exp. 45 | $N_2$ atm. | 99.6 | 89 |

EXAMPLE 30

Synthesis of Tricyclic Ketone

Whole synthetic processes of tricyclic ketone (h) starting from Compound (l) are given below;

(1) Synthesis of Compound (m)

To a stirred mixture of Compound (l) (20.0 g, 56.0 mmol, 2 eq., content: 93.9%), triethylsilane (17.9 mL, 112 mmol, 2 eq.) and crotyl alcohol (15.7 mL, 184.8 mmol, 3.3 eq.), trifluoroacetic acid (28.5 mL, 375.2 mmol, 6.7 eq.) was added dropwise at 0–5° C. under nitrogen atmosphere and the mixture was stirred at the temperature for 30 min. The mixture was stirred at ambient temperature for 20 hrs and then an aqueous solution of sodium carbonate (20.8 g in 277 mL of water) and n-hexane (56 mL) were added to the mixture. The organic layer was separated and the aqueous layer was extracted with n-hexane (57 mL). The combined organic layers were evaporated under reduced pressure to dryness. The residue was purified through silica gel column chromatography; silica gel (80 g, Fuji Silysia PSQ100B), eluent; n-hexane-ethyl acetate (73:3) to remove byproduct, Compound (v) (4.95 g, 14.68 mmol, purity 98.43%, yield 26%). Compound (m); 17.8 g (64% yield), content: 80.0% by HPLC (see Example 17).

¹H-NMR (400 MHz, CDCl₃) δ: 0.24 (9H, s, TMS), 1.69 (3H, dd, J=1.0, 6.1 Hz, =CHC$\underline{H}_3$), 3.85–4.05 (2H, m, OC$\underline{H}_2$CH=), 3.93 (3H, s, CH₃O), 4.55 (2H, s, OCH₂), 5.55–5.83 (2H, m, CH=CH), 7.4 7(1H, s).

Compound (v); 5.0 g (26% yield), content: 98.4% (HPLC).

¹H-NMR (400 MHz, CDCl₃) δ: 0.27 (9H, s, TMS), 2.45 (1H, t, J=6.8 Hz, OH), 3.99 (3H, s, CH₃O), 4.79 (2H, d, J=6.8 Hz, C$\underline{H}_2$OH), 7.49 (1H, s).

(2) Synthesis of Compound (n)

A mixture of Compound (m) (1.27 g, 2.56 mmol, content: 78.73%), tetrabutylammonium bromide (0.82 g, 2.56 mmol) and palladium acetate (57 mg, 0.26 mmol) in a mixture of diisopropyl ether-acetonitrile-water (4:3:1, 20 mL) was heated under reflux for 30 min. After cooling the inner temperature to 20° C. or below, the insoluble material of the mixture was removed by filtration and the material was washed with n-hexane (10 mL). The filtrate and the washing were combined and to the solution, n-hexane (10 mL) and 10% sodium sulfite (16 mL, 113 mmol, 5 eq.) were added. The organic layer of the mixture was separated and washed with 1 N hydrochloric acid (16.4 mL) and water (10 mL×2), successively. The organic layer was evaporated under reduced pressure to dryness. Compound (n): brown oil, 0.83 g (91% yield), content: 73.34% by HPLC, endo-exo ratio: 10.6 by HPLC (see Example 17).

$^1$H-NMR (400 MHz, CDCl$_3$) δ: 0.26 (9H, s, TMS), 1.12 (3H, t, J=7.3 Hz, CH$_2$C$\underline{H}_3$), 2.31 (2H, dq, J=1.0, 7.3 Hz, C$\underline{H}_2$CH$_3$), 3.94 (3H, s, OCH$_3$), 5.00 (2H, s, OCH$_2$), 6.51 (1H, t, J=1.0 Hz, OCH=), 6.83 (1H, s, aromatic-H).

(3) Synthesis of Compound (o)

To a solution of potassium ferricyanide (195.7 g, 0.59 mol), potassium carbonate (82.1 g, 0.59 mol) and methanesulfonamide (37.7 g, 0.40 mol) in water (990 mL), (DHQD)$_2$PYR (4.36 g, 4.95 mmol) and potassium osmate (VI) dihydrate (0.99 mmol) were added and the mixture was stirred at around 5° C. for 1 hr. To the mixture, Compound (n) (77.8 g, 0.18 mol, content: 61.5%) was added and the resulting mixture was stirred at around 5° C. for 20 hrs and then powdered sodium sulfite (74.9 g) was added. The suspension was stirred at around 5° C. for 30 mn and the insoluble material was filtered on a Celite pad. The material on the pad was washed with ethyl acetate (4 times, total 770 mL). The organic layer of the filtrate was separated and the aqueous layer was further extracted with ethyl acetate (770 mL). The combined organic layers were dried over anhydrous sodium sulfate and evaporated under reduced pressure to dryness. The residue was purified through silica gel column chromatography; silica gel (700 g, Fuji Silysia PSQ100B), eluent: dichloromethane-ethyl acetate (4:1). Compound (o): umber solid.

(4) Synthesis of Compound (p)

A mixture of Compound (o) (70.2 g), iodine (183.7 g, 0.72 mol) and calcium carbonate (36.23 g, 0.36 mol) in methanol-water (10:1, 1.0 L) was heated under reflux for 5 hrs. After cooling, 10% sodium sulfite (1.0 L) and chloroform (1.0 L) were added to the mixture and the resulting mixture was stirred at ambient temperature for 15 min. The insoluble material was filtered by suction and the material was washed with chloroform (0.5 L). The combined organic layers of the filtrate and the washing were separated and the aqueous layer was further extracted with chloroform (0.5 L). The combined organic layers were dried over anhydrous sodium sulfate, filtered and evaporated under reduced pressure to dryness. Compound (p): umber oil, 53.6 g (overall 81% yield from Compound (m)), content: 80.4% by HPLC (see Example 22), 96.2% ee by chiral HPLC (see Example 22).

$^1$H-NMR (400 MHz, CDCl$_3$) δ: 0.28 (9H, s, TMS), 0.94 (3H, t, J=7.4 Hz, CH$_2$C$\underline{H}_3$), 1.76 (2H, q, J=7.4 Hz, C$\underline{H}_2$CH$_3$), 3.61 (1H, s, OH), 3.98 (3H, s, OCH$_3$), 5.23 (1H, d, J=15.6 Hz,), 5.54 (1H, d, J=15.6 Hz), 7.33 (1H, s, aromatic-H).

(5) Synthesis of Compound (q)

A mixture of Compound (p) (50.2 g, 0.14 mol, content: 80.4%, 96.2% ee), N-chlorosuccinimide (107.36 g, 0.80 mol) and sodium iodide (120.52 g, 0.80 mol) in acetic acid (411 mL) was warmed at about 65° C. with stirring for 16 hrs. After cooling, 20% sodium carbonate (1.7 L), 10% sodium sulfite (1.0 L) and chloroform (0.6 L) were added, successively, to the mixture. The organic layer of the mixture was separated and the aqueous layer was extracted with chloroform (0.6 L×2). The combined organic layers were dried over anhydrous sodium sulfate, filtered, and then evaporated under reduced pressure to dryness (crude q).

(6) Purification of Compound (q) (1)

A suspension of crude Compound (q) (the residue of the previous step, purity: 89.2% by HPLC) in methanol (150 mL) was added dropwise to 0.2 N sodium hydroxide (0.40 mol) with stirring. The mixture was stirred at ambient temperature for 2 hrs. The alkaline mixture was washed with chloroform (400 mL×3) and the aqueous layer was separated and adjusted the pH to 1–2 with 6 N hydrochloric acid. The acidic solution was extracted with chloroform (400 mL×3). The organic layer was separated and dried over anhydrous sodium sulfate, filtered and then evaporated under reduced pressure to dryness. Semi-purified (q), purity: 97.7% by HPLC (see Example 25).

(7) Purification of Compound (q) (2)

Semi-purified (q) was dissolved in chloroform (280 mL) and n-hexane (400 mL) was added on the surface of the solution and the resulting mixture was placed at ambient temperature for 15 hrs. The precipitate was removed by filtration and the filtrate was evaporated under reduced pressure to dryness. Compound (q); liver oil, 47.4 g (86% yield), content: 84.5% by HPLC (see Example 25), 99.7% ee by chiral HPLC (see Example 25).

$^1$H-NMR (400 MHz, CDCl$_3$) δ: 0.94 (3H, t, J=7.3 Hz, CH$_2$C$\underline{H}_3$), 1.75 (2H, q, J=7.3 Hz, C$\underline{H}_2$CH$_3$), 3.58 (1H, s, OH), 3.96 (3H, s, OCH$_3$), 5.16 (1H, d, J=15.6 Hz), 5.47 (1H, d, J=15.6 Hz), 7.59 (1H, s, aromatic-H). [α]$_D^{20}$=+51.3 (c=0.981, CHCl$_3$)

(8) Synthesis of Compound (r)

A solution of Compound (q) (42.8 g, 0.10 mol, content: 84.5%), palladium acetate (1.34 g, 5.95 mmol) and potassium carbonate (24.67 g, 0.179 mol) in propanol (490 mL) was degassed by suction and replaced with argon gas and degassed by suction and then charged with carbon monoxide. The mixture was stirred at 60° C. for 4 hrs. After cooling, the insoluble material was removed on a Celite pad and the material on the pad was washed with ethyl acetate (300 mL). The filtrate was washed with 1 N hydrochloric acid (150 mL) and brine (300 mL) and the aqueous layer was separated and extracted with ethyl acetate (300 mL). The combined organic layers were dried over anhydrous sodium sulfate, filtered and then evaporated under reduced pressure to dryness. The residue was purified through silica gel column chromatography; silica gel (200 g), eluent: chloroform-methanol (99:1). Compound (r): brown oil, 30.3 g (70% yield), content: 73.4% by HPLC (see Example 26).

$^1$H-NMR (400 MHz, CDCl$_3$) δ: 0.88 (3H, t, J=7.3 Hz, CH$_3$), 1.04 (3H, t, J=7.3 Hz, CH$_3$), 1.82 (4H, m, CH$_2$×2), 3.69 (1H, s, OH), 4.09 (3H, s, OCH$_3$), 4.34 (2H, t, J=6.8 Hz, CH$_2$), 5.31 (1H, d, J=16.3 Hz), 5.61 (1H, d, J=16.3 Hz), 7.94 (1H, s, aromatic-H)

(9) Synthesis of Compound (s)

To a stirred solution of Compound (r) (28.7 g, 68.2 mmol, content: 73.4%) and sodium iodide (27.6 g, 0.18 mol) in absolute acetonitrile (141 mL), chlorotriethylsilane (23.3 mL, 0.18 mmol) was added dropwise at ambient temperature under nitrogen atmosphere. The mixture was stirred at ambient temperature for 3 hrs and then quenched by 1 N hydrochloric acid (8 mL) and 10% sodium sulfite (232 mL). The resulting mixture was stirred at ambient temperature for 30 min. The mixture was extracted with ethyl acetate and the organic layer was separated and evaporated under reduced pressure to dryness. Compound (s): 22.3 g (95% yield), content: 85.6% by HPLC (see Example 27).

$^1$H-NMR (400 MHz, CDCl$_3$) δ: 1.00 (3H, t, J=7.3 Hz, CH$_3$), 1.02 (3H, t, J=7.3 Hz, CH$_3$), 1.83 (4H, m, CH2×2), 3.75 (1H, s, OH), 4.35 (2H, t, J=6.8 Hz, CH$_2$), 5.21 (1H, d, J=17.1 Hz), 5.61 (1H, d, J=17.1 Hz), 7.28 (1H, s, aromatic-H), 9.59 (1H, brs, OH).

(10) Synthesis of Compound (t)

A solution of Compound(s) (0.50 g, 1.46 mmol, content: 86.6%) and potassium carbonate (0.40 g, 2.92 mmol) in dimethylsulfoxide (7 mL) was stirred at 50° C. under argon atmosphere for 20 min. To the stirred mixture, tert-butyl acrylate (2.1 mL, 14.6 mmol) was added dropwise under argon atmosphere and the stirring was continued for 20 hrs. Water (10 mL) and concentrated hydrochloric acid (1 mL) were added dropwise to the stirred mixture in an ice-cooled bath. The mixture was extracted with toluene-ethyl acetate (4:1, 7 mL×4). The combined extracts were washed with water (5 mL×3), dried over anhydrous sodium sulfate, filtered and then evaporated under reduced pressure to dryness. Compound (t): 0.55 g (77% yield), content: 75.0% by HPLC (see Example 28).

$^1$H-NMR (400 MHz, CDCl$_3$) δ: 0.99 (3H, t, J=7.4 Hz, CH$_2$CH$_3$), 1.58 (9H, 8, t-Bu), 1.83 (2H, m, CH$_2$CH$_3$), 4.68 (2H, S, CH$_2$), 5.25 (1H, d, J=17.8 Hz), 5.69 (1H, d, J=17.8 Hz), 7.01 (1H, s, aromatic-H).

(11) Synthesis of Compound (h)

To a solution of Compound (t) (1.02 g, 1.84 mmol, content: 66.0%) in toluene (17 mL), trifluoroacetic acid (1.7 mL) was added with stirring under argon atmosphere. The mixture was stirred at 110° C. under argon atmosphere for 100 min. After cooling, the mixture was evaporated under reduced pressure to dryness. The residue was suspended in dichloromethane (50 mL) and the insoluble material was filtered on a Celite pad. The filtrate was washed with water (10 mL) and the organic layer was separated and the aqueous layer was extracted with dichloromethane (20 mL×3). The combined extracts were dried over anhydrous sodium sulfate, filtered and evaporated under reduces pressure to dryness. Compound (h); (s)-4-ethyl-7,8-dihydro-4-hydroxy-1H-pyrano-[3,4-f]indolidine-3,6,10(4H)-trione; 0.46 g (77% yield), content: 80.7% by HPLC (as follows).

$^1$H-NMR (400 MHz, CDCl$_3$) δ: 0.98 (3H, t, J=7.3 Hz, CH$_2$CH$_3$), 1.81 (2H, m, CH$_2$CH$_3$), 2.97 (2H, t, J=6.3 Hz, CH$_2$CH$_2$), 3.64 (1H, s, OH), 4.34 (2H, m, CH$_2$CH$_3$), 5.25 (1H, d, J=17.1 Hz), 5.68 (1H, d, J=17.1 Hz), 7.22 (1H, s, aromatic-H).

HPLC Operating Conditions
Column: Inertsil ODS-2, 0.46 cm ID×25 cm
Temperature: constant temperature at around 40° C.
Flow rate: 1 mL/min
Mobile phase: 10 mM potassium dihydrogenphosphate-methanol (4:1)
Detect: 254 nm

EXAMPLE 31

Synthesis of 7-ethyl-10-hydroxycamptothecin (SN-38)

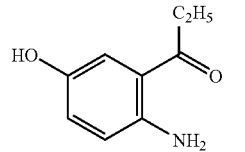

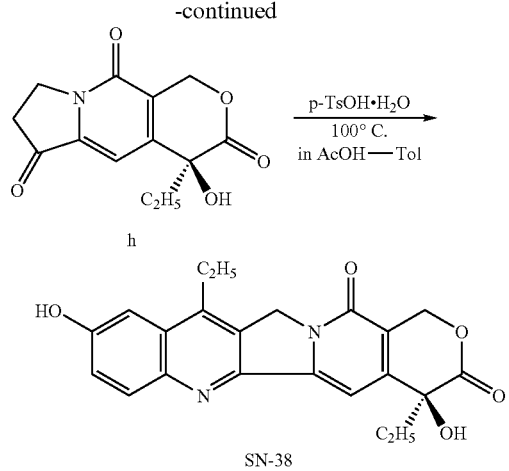

A suspension of Compound (h) (0.50 g, 1.82 mmol, content: 96.6%), obtained as described in Example 30 (11), and Compound (e) (0.36 g, 2.14 mmol) in the presence of p-toluenesulfonic acid monohydrate (10 mg) in acetic acid-toluene (1:1, 10 mL) was stirred at 100° C. under nitrogen gas atmosphere for 18 hrs. The mixture was evaporated under reduced pressure and toluene (10 mL) was added to the residue and then evaporated under reduced pressure to dryness. The residue was suspended in acetone (9 mL) and the suspension was stirred at ambient temperature for 2 hrs. The suspension was filtered by suction and the collected solid was washed with acetone (2 mL×2) and then dried under reduced pressure. SN-38: brown solid, 0.63 g (89% yield), content: 97.7% by HPLC (see Example 9).

$^1$H-NMR (400 MHz, CDCl$_3$) δ: 0.98 (3H, t, J=7 Hz, CH$_3$), 1.38 (3H, t, J=7 Hz, CH$_3$), 1.90 (2H, q, J=7 Hz, CH$_2$), 3.08 (2H, q, J=7 Hz, CH$_2$), 5.17 (2H, s, CH$_2$O), 5.23 (1H, d, J=16 Hz), 5.54 (1H, d, J=16 Hz), 7.34–7.39 (3H, m), 6.83 (1H, d, J=9 Hz).

EXAMPLE 32

Synthesis of 7-ethyl-10-[4-(1-piperidino)-1-piperidino]carbonyloxycamptothecin (SN-38B-11)

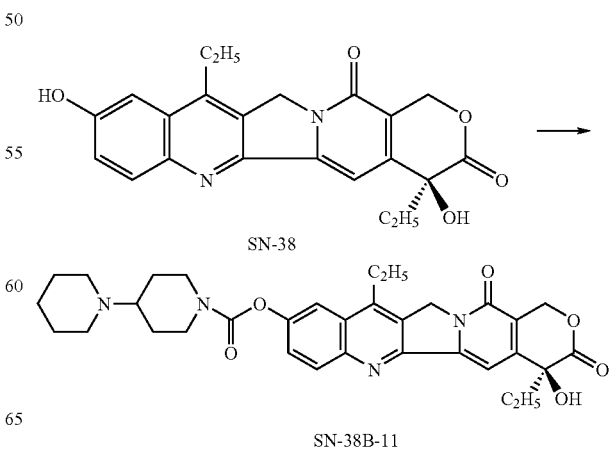

SN-38 (0.91 g, 2.32 mmol), obtained as described in Example 31, was converted into SN-38B-11 (1.22 g, 89% yield, 99.8% ee by the chiral HPLC conditions; see Example 10) by the reported method (S. Sawada, et al., Chem. Pharm. Bull., 1991, 39, 1446).

EXAMPLE 33

Synthesis of 7-ethyl-10-[4-(1-piperidino)-1-piperidino]carbonyloxycamptothecin hydrochloride trihydrate (CPT-11)

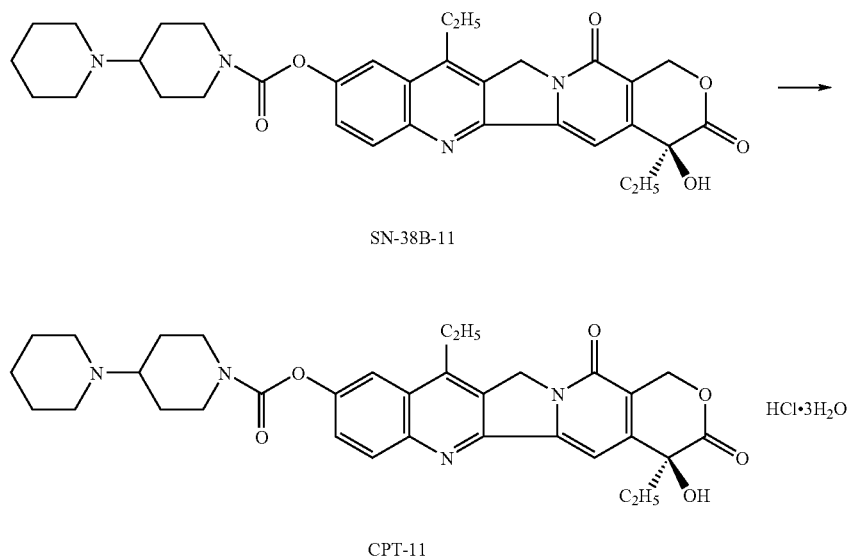

SN-38B-11 (1.00 g, 1.7 mmol), obtained as described in Example 32, was dissolved in 0.1 N hydrochloric acid (20 mL) by heating at around 80° C. Acetonitrile (100 mL) was added to the solution and the mixture was gently stirred at ambient temperature for 15 hrs. The precipitates were filtered by suction and dried under reduced pressure and then humidified. CPT-11: pale yellow crystalline powder, 0.95 mg (89.9% yield).

INDUSTRIAL APPLICABILITY

By use of the synthetic process of the invention highly pure 2'-amino-5'-hydroxypropiophenone and tricyclic ketone can be synthesized in a short time with a high recovery yield, and by use of these as intermediates a total synthesis of CPT analogs can efficiently be carried out.

The invention claimed is:

1. A process for preparing a tricyclic ketone to synthesize camptothecin analogs, wherein from Compound (k):

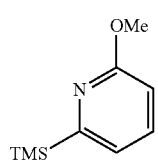

(wherein TMS is a trimethylsilyl group, and Me is a methyl group), or Compound (v):

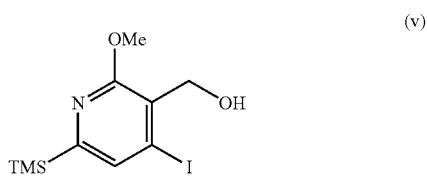

(wherein TMS is a trimethylsilyl group, and Me is a methyl group), Compound (l):

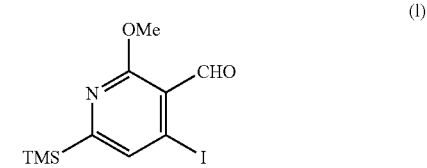

(wherein TMS is a trimethylsilyl group, and Me is a methyl group)

is produced; and from Compound (l) Compound (m):

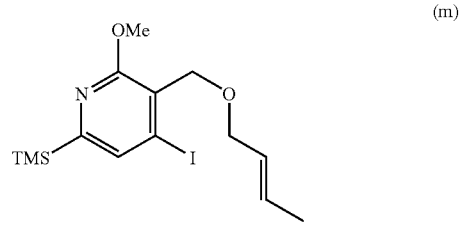

(wherein TMS is a trimethylsilyl group, and Me is a methyl group)

is produced; and from Compound (m) Compound (n):

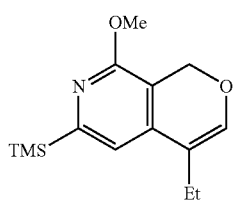
(n)

(wherein TMS is a trimethylsilyl group, Me is a methyl group, and Et is an ethyl group)
is produced; and from Compound (n) Compound (o):

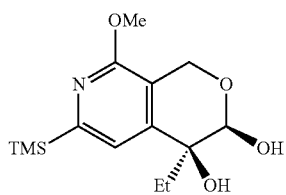
(o)

(wherein TMS is a trimethylsilyl group, Me is a methyl group, and Et is an ethyl group)
is produced; and from Compound (o) Compound (p):

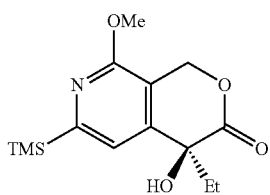
(p)

(wherein TMS is a trimethylsilyl group, Me is a methyl group, and Et is an ethyl group)
is produced; and from Compound (p) Compound (q):

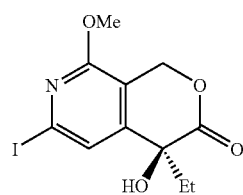
(q)

(wherein Me is a methyl group, and Et is an ethyl group)
is produced; and from Compound (q) Compound (r):

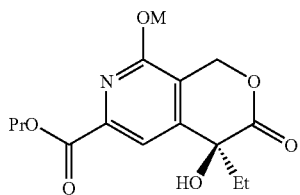
(r)

(wherein Me is a methyl group, Et is an ethyl group, and Pr is a propyl group)

is produced; and from Compound (r) Compound (s):

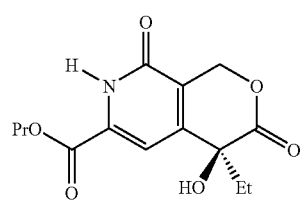
(s)

(wherein Et is an ethyl group, and Pr is a propyl group)
is produced; and from Compound (s) Compound (t):

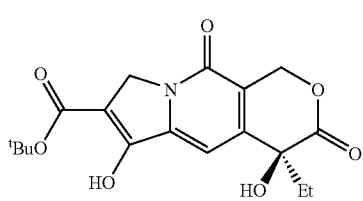
(t)

(wherein Et is an ethyl group, and tBu is a t-butyl group)
is produced; and from Compound (t) Compound (h):

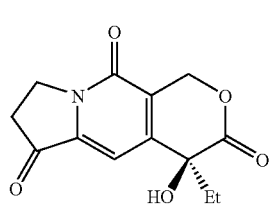
(h)

(wherein Et is an ethyl group)
is produced, wherein the improvement comprises
(1) a step to obtain Compound (l) that comprises mixing Compound (k), a lithiating agent, a formylation reagent and an iodination reagent.

2. A process according to claim 1, wherein in the step (1) the lithiating agent is n-butyl lithium.

3. A process according to claim 1, wherein in the step (1) the reaction temperature is the constant temperature of −30 to −40° C.

4. A process according to claim 1, wherein Compound (q) is purified chemically by purification steps consisting of;
a step to add the reaction product obtained by the step to produce Compound (q) from Compound (p) to an aqueous alkaline solution and to stir;
a step to add an organic solvent and to stir, followed by removal of the organic layer; and
a step to make the aqueous layer acidic and to extract with an organic solvent.

5. A process according to claim 4, wherein the aqueous alkaline solution is an aqueous sodium hydroxide solution.

6. A process according to claim 4, wherein the organic solvent is chloroform.

7. A process according to claim 1, wherein Compound (q) is purified optically by purification steps consisting of;
  a step to dissolve the reaction product obtained by the step to produce Compound (q) from Compound (p) in a high polarity solvent, followed by lamination of a low polarity solvent; and
  a step to filter a precipitate which is followed by concentration of the filtrate to dryness under reduced pressure.

8. A process according to claim 7, wherein the high polarity solvent is chloroform.

9. A process according to claim 7, wherein the low polarity solvent is n-hexane.

10. A process for preparing camptothecin analogs, wherein the tricyclic ketone, which is obtained by the process according to claim 1, is reacted with 2'-amino-5'-hydroxypropiophenone.

11. A process according to claim 10, wherein the tricyclic ketone and 2'-amino-5'-hydroxypropiophenone are mixed, and said mixture is reacted under an inert gas atmosphere.

12. A process according to claim 1, further comprising (2) a step to obtain Compound (m) that comprises mixing Compound (l), crotyl alcohol, triethylsilane and an acid, and reacting said mixture without use of solvent.

13. A process according to claim 12, further comprising (3) a step to obtain Compound (l) that comprises mixing Compound (v) obtained as a byproduct in the step (2), with an oxidizing agent and a base.

14. A process according to claim 13, wherein in the step (3) the oxidizing agent is TEMPO-sodium hypochlorite.

15. A process according to claim 1, further comprising (4) a step to obtain Compound (n) that comprises mixing Compound (m), a palladium catalyst, a base and a phase-transfer catalyst, and refluxing said mixture in solvent.

16. A process according to claim 15, wherein in the step (4) the base is potassium carbonate or diisopropylethylamine.

17. A process according to claim 15, wherein in the step (4) the solvent is tetrahydrofuran, or a diisopropyl ether-acetonitrile-water mix liquid.

18. A process according to claim 1, further comprising (5) a step to obtain Compound (o) that comprises mixing Compound (n), an osmium catalyst, a co-oxidizing agent, a base and an asymmetric reagent.

19. A process according to claim 18, wherein in the step (5) the osmium catalyst is potassium osmate(VI).

20. A process according to claim 1, further comprising (6) a step to obtain Compound (p) that comprises mixing Compound (o), a base and iodine, and refluxing said mixture in an alcohol-water mix liquid.

21. A process according to claim 20, wherein in step (6) the mole ratio of the iodine to Compound (o) is 4:1.

22. A process according to claim 1, further comprising (7) a step to obtain Compound (q) that comprises mixing Compound (p) and a desilylation-iodination reagent.

23. A process according to claim 22, wherein in the step (7) the desilylation-iodination reagent is iodine-silver trifluoroacetate or N-chlorosuccinimide-sodium iodide.

24. A process according to claim 1, further comprising (8) a step to obtain Compound (r) that comprises mixing Compound (q), a palladium catalyst and a base, and reacting said mixture in 1-propanol under a carbon monoxide gas atmosphere.

25. A process according to claim 1, further comprising (9) a step to obtain Compound (s) that comprises mixing Compound (r) and a demethylation reagent, and reacting said mixture at room temperature.

26. A process according to claim 1, further comprising (10) a step to obtain Compound (t) that comprises reacting Compound (s) under the presence of t-butyl acrylate and a base.

27. A process according to claim 26, wherein in the step (10) the base is potassium carbonate.

* * * * *

UNITED STATES PATENT AND TRADEMARK OFFICE
CERTIFICATE OF CORRECTION

PATENT NO. : 7,126,000 B2
APPLICATION NO. : 10/467987
DATED : October 24, 2006
INVENTOR(S) : Takanori Ogawa et al.

It is certified that error appears in the above-identified patent and that said Letters Patent is hereby corrected as shown below:

Column 1, line 57, please delete the word "racememate" and replace it with the word -- racemate --;

Column 11, line 53, please delete the word "a" and replace it with the word -- an --;

Column 13, line 20, please delete the word "acetnitrile" and replace it with the word -- acetonitrile --;

Column 21, lines 31, 36 and 42, please delete the word "litiation" and replace it with the word -- lithiation -- in each instance;

Column 22, line 14, please delete the word "by product" and replace it with the word -- byproduct --;

Column 22, line 15, please delete the word "insolvent" and replace it with the word -- in solvent --;

Column 22, line 19, please delete the word "actonitrile" and replace it with the word -- acetonitrile --;

Column 22, line 51, please delete the word "tertrahydrofuran" and replace it with the word -- tetrahydrofuran --;

Column 23, line 34, please delete the word "methymorpholine" and replace it with the word -- methylmorpholine --;

Column 27, line 49, please delete the word "forth" and replace it with the words -- for the --;

Column 32, line 66, please delete the word "mol" and replace it with the word -- mmol --;

Column 35, please replace the existing formula legend with the following formula legend -- "p-TsOH·$H_2$O --;

Column 37, line 4, please delete the word "cabonyloxycamptothecin" and replace it with the word -- carbonyloxycamptothecin --;

UNITED STATES PATENT AND TRADEMARK OFFICE
CERTIFICATE OF CORRECTION

PATENT NO. : 7,126,000 B2
APPLICATION NO. : 10/467987
DATED : October 24, 2006
INVENTOR(S) : Takanori Ogawa et al.

It is certified that error appears in the above-identified patent and that said Letters Patent is hereby corrected as shown below:

Column 43, lines 1 and 3, please delete the surname "Josein" and replace it with the surname -- Josien -- in each instance;

Column 44, line 34, please delete the word "acatate" and replace it with the word -- acetate --;

Column 45, line 66, please delete the word "fericyanide" and replace it with the word -- ferricyanide --;

Column 46, line 4, please delete the word "aroud" and replace it with the word -- around --;

Column 46, line 22, please delete the words "enantio excess" and replace it with the word -- enantioexcess --;

Column 46, lines 31 and 33, please delete the surname "Josein" and replace it with the surname -- Josien -- in each instance;

Column 49, line 21, please delete the word "dihydrogenphophate" and replace it with the word -- dihydrogenphosphate --;

Column 52, line 2, please delete the word "azeotoropic" and replace it with the word -- azeotropic --;

Column 53, line 24, please delete the word "30 mm" and replace it with the word -- 30 min --;

Column 55, line 23, please delete the formula "(9H, 8, t-Bu)" and replace it with the formula -- (9H, s, t-Bu) --;

Column 55, line 39, please delete "(s)" and replace it with -- *(S)* --;

UNITED STATES PATENT AND TRADEMARK OFFICE
CERTIFICATE OF CORRECTION

PATENT NO.       : 7,126,000 B2
APPLICATION NO.  : 10/467987
DATED            : October 24, 2006
INVENTOR(S)      : Takanori Ogawa et al.

It is certified that error appears in the above-identified patent and that said Letters Patent is hereby corrected as shown below:

In claim 1, column 59, at compound "(r)", please delete the group "OM" and replace it with the group -- OMe --;

Signed and Sealed this

Twenty-first Day of August, 2007

JON W. DUDAS
*Director of the United States Patent and Trademark Office*